(12) United States Patent
Bhullar et al.

(10) Patent No.: US 8,551,308 B2
(45) Date of Patent: *Oct. 8, 2013

(54) BIOSENSOR AND METHOD OF MAKING

(75) Inventors: Raghbir S. Bhullar, Indianapolis, IN (US); Eric R. Diebold, Fishers, IN (US); Brian S. Hill, Avon, IN (US); Nigel Surridge, Carmel, IN (US); Paul Douglas Walling, Indianapolis, IN (US)

(73) Assignees: Roche Diagnostics Operations, Inc., Indianapolis, IN (US); Roche Operations Ltd., Hamilton (BM)

( * ) Notice: Subject to any disclaimer, the term of this patent is extended or adjusted under 35 U.S.C. 154(b) by 1296 days.

This patent is subject to a terminal disclaimer.

(21) Appl. No.: 12/238,101

(22) Filed: Sep. 25, 2008

(65) Prior Publication Data
US 2009/0056120 A1 Mar. 5, 2009

Related U.S. Application Data

(60) Division of application No. 10/871,937, filed on Jun. 18, 2004, now abandoned, which is a continuation-in-part of application No. 10/601,144, filed on Jun. 20, 2003, now Pat. No. 7,073,246, which is a continuation-in-part of application No. 10/264,891, filed on Oct. 4, 2002, now Pat. No. 7,276,146, which is a continuation-in-part of application No. 09/840,843, filed on Apr. 24, 2001, now Pat. No. 6,767,440, which is a continuation-in-part of application No. 09/684,257, filed on Oct. 6, 2000, now Pat. No. 6,645,359, which is a continuation-in-part of application No. 09/411,940, filed on Oct. 4, 1999, now Pat. No. 6,662,439.

(51) Int. Cl.
*G01N 27/327* (2006.01)
*C12Q 1/25* (2006.01)
*H05K 3/00* (2006.01)

(52) U.S. Cl.
USPC ... 204/403.01; 205/775; 205/792; 205/777.5; 29/825; 29/846; 29/847

(58) Field of Classification Search
USPC ............ 204/403.01–403.15; 205/775, 777.5, 205/778, 792; 29/825, 846, 847; 219/121.12, 219/121.11, 121.18, 121.19
See application file for complete search history.

(56) References Cited

U.S. PATENT DOCUMENTS

| | | | |
|---|---|---|---|
| 3,715,192 | A | 2/1973 | Wenz et al. |
| 3,980,437 | A | 9/1976 | Kishimoto et al. |

(Continued)

FOREIGN PATENT DOCUMENTS

| | | | |
|---|---|---|---|
| CN | 1 467 496 A | | 5/2003 |
| DE | 3 922 478 A1 | | 1/1991 |

(Continued)

OTHER PUBLICATIONS

Osamu Niwa, "Fabrication and characteristics of vertically separated interdigitated array electrodes", Journal of Electroanalytical Chemistry, Aug. 10, 1989, pp. 291-297, vol. 267.

(Continued)

*Primary Examiner* — J. Christopher Ball
*Assistant Examiner* — Jennifer Dieterle
(74) *Attorney, Agent, or Firm* — Woodard, Emhardt, Moriarty, McNett & Henry LLP

(57) ABSTRACT

An electrochemical biosensor with electrode elements that possess smooth, high-quality edges. These smooth edges define gaps between electrodes, electrode traces and contact pads. Due to the remarkable edge smoothness achieved with the present invention, the gaps can be quite small, which provides marked advantages in terms of test accuracy, speed and the number of different functionalities that can be packed into a single biosensor. Further, the present invention provides a novel biosensor production method in which entire electrode patterns for the inventive biosensors can be formed all at one, in nanoseconds—without regard to the complexity of the electrode patterns or the amount of conductive material that must be ablated to form them.

11 Claims, 20 Drawing Sheets

(56) References Cited

U.S. PATENT DOCUMENTS

| | | | |
|---|---|---|---|
| 4,065,263 A | 12/1977 | Woodbridge, III | |
| 4,225,410 A | 9/1980 | Pace | |
| 4,420,564 A | 12/1983 | Tsuji et al. | |
| 4,476,149 A | 10/1984 | Poppe et al. | |
| 4,510,383 A | 4/1985 | Ruppender | |
| 4,545,382 A | 10/1985 | Higgins et al. | |
| 4,571,292 A | 2/1986 | Liu et al. | |
| 4,578,716 A | 3/1986 | Van Rijckevorsel et al. | |
| 4,592,893 A | 6/1986 | Poppe et al. | |
| 4,671,288 A | 6/1987 | Gough | |
| 4,679,562 A | 7/1987 | Luksha | |
| 4,714,874 A | 12/1987 | Morris et al. | |
| 4,789,804 A | 12/1988 | Karube et al. | |
| 4,797,256 A | 1/1989 | Watlington, IV | |
| 4,805,624 A | 2/1989 | Yao et al. | |
| 4,877,580 A | 10/1989 | Aronowitz et al. | |
| 4,897,173 A | 1/1990 | Nankai et al. | |
| 4,927,516 A | 5/1990 | Yamaguchi et al. | |
| 4,935,105 A | 6/1990 | Churchouse | |
| 4,938,860 A | 7/1990 | Wogoman | |
| 4,970,145 A | 11/1990 | Bennetto et al. | |
| 5,049,487 A | 9/1991 | Phillips et al. | |
| 5,059,394 A | 10/1991 | Phillips et al. | |
| 5,066,372 A | 11/1991 | Wetall | |
| 5,104,480 A | 4/1992 | Wojnarowski et al. | |
| 5,120,420 A | 6/1992 | Nankai et al. | |
| 5,122,244 A | 6/1992 | Hoenes et al. | |
| 5,141,850 A | 8/1992 | Cole et al. | |
| 5,141,868 A | 8/1992 | Shanks et al. | |
| 5,143,694 A | 9/1992 | Schafer et al. | |
| 5,179,005 A | 1/1993 | Phillips et al. | |
| 5,187,100 A | 2/1993 | Matzinger et al. | |
| 5,192,415 A | 3/1993 | Yoshioka et al. | |
| 5,243,516 A | 9/1993 | White | |
| 5,250,439 A | 10/1993 | Musho et al. | |
| 5,264,103 A | 11/1993 | Yoshioka et al. | |
| 5,266,179 A | 11/1993 | Nankai et al. | |
| 5,281,395 A | 1/1994 | Markart et al. | |
| 5,286,362 A | 2/1994 | Hoenes et al. | |
| 5,288,636 A | 2/1994 | Pollmann et al. | |
| 5,296,192 A | 3/1994 | Carroll et al. | |
| 5,304,468 A | 4/1994 | Phillips et al. | |
| 5,306,623 A | 4/1994 | Kiser et al. | |
| 5,344,754 A | 9/1994 | Zweig | |
| 5,366,609 A | 11/1994 | White et al. | |
| 5,379,214 A | 1/1995 | Arbuckle et al. | |
| 5,382,346 A | 1/1995 | Uenoyama et al. | |
| 5,385,846 A | 1/1995 | Kuhn et al. | |
| 5,389,215 A | 2/1995 | Horiuchi et al. | |
| 5,395,504 A | 3/1995 | Saurer et al. | |
| 5,413,690 A | 5/1995 | Kost et al. | |
| 5,413,764 A | 5/1995 | Haar | |
| 5,418,142 A | 5/1995 | Kiser et al. | |
| 5,421,189 A | 6/1995 | Dussault | |
| 5,424,035 A | 6/1995 | Hones et al. | |
| 5,426,032 A | 6/1995 | Phillips et al. | |
| 5,437,999 A | 8/1995 | Diebold et al. | |
| 5,438,271 A | 8/1995 | White et al. | |
| 5,439,826 A | 8/1995 | Kontorovich | |
| 5,465,480 A | 11/1995 | Karl et al. | |
| 5,469,846 A | 11/1995 | Khan | |
| 5,470,533 A | 11/1995 | Shindo et al. | |
| 5,494,638 A | 2/1996 | Gullick | |
| 5,496,453 A | 3/1996 | Uenoyama et al. | |
| 5,508,171 A | 4/1996 | Walling et al. | |
| 5,509,410 A | 4/1996 | Hill et al. | |
| 5,515,170 A | 5/1996 | Matzinger et al. | |
| 5,526,120 A | 6/1996 | Jina et al. | |
| 5,533,393 A | 7/1996 | Bonne et al. | |
| 5,547,702 A | 8/1996 | Gleisner | |
| 5,552,116 A | 9/1996 | Yokota et al. | |
| 5,554,531 A | 9/1996 | Zweig | |
| 5,563,042 A | 10/1996 | Phillips et al. | |
| 5,569,608 A | 10/1996 | Sommer | |
| 5,575,895 A | 11/1996 | Ikeda et al. | |
| 5,575,930 A | 11/1996 | Tetje-Girault et al. | |
| 5,576,073 A | 11/1996 | Kickelhain | |
| 5,580,794 A | 12/1996 | Allen | |
| 5,582,697 A | 12/1996 | Ikeda et al. | |
| 5,589,326 A | 12/1996 | Deng et al. | |
| 5,593,739 A | 1/1997 | Kickelhain | |
| 5,597,532 A | 1/1997 | Connolly | |
| 5,605,837 A | 2/1997 | Karimi et al. | |
| 5,620,579 A | 4/1997 | Genshaw et al. | |
| 5,620,863 A | 4/1997 | Tomasco et al. | |
| 5,627,075 A | 5/1997 | Bateson | |
| 5,628,890 A | 5/1997 | Carter et al. | |
| 5,645,798 A | 7/1997 | Schreiber et al. | |
| 5,650,062 A | 7/1997 | Ikeda et al. | |
| 5,653,863 A | 8/1997 | Genshaw et al. | |
| 5,656,502 A | 8/1997 | MacKay et al. | |
| 5,658,443 A | 8/1997 | Yamamoto et al. | |
| 5,665,215 A | 9/1997 | Bussmann et al. | |
| 5,670,031 A | 9/1997 | Hintsche et al. | |
| 5,682,884 A | 11/1997 | Hill et al. | |
| 5,691,486 A | 11/1997 | Behringer et al. | |
| 5,695,623 A | 12/1997 | Michel et al. | |
| 5,708,247 A | 1/1998 | McAleer et al. | |
| 5,720,862 A | 2/1998 | Hamamoto et al. | |
| 5,723,284 A | 3/1998 | Ye | |
| 5,727,548 A | 3/1998 | Hill et al. | |
| 5,755,953 A | 5/1998 | Henning et al. | |
| 5,757,666 A | 5/1998 | Schreiber et al. | |
| 5,759,364 A | 6/1998 | Charlton et al. | |
| 5,762,770 A | 6/1998 | Pritchard et al. | |
| 5,773,319 A | 6/1998 | Chu et al. | |
| 5,780,304 A | 7/1998 | Matzinger et al. | |
| 5,788,833 A | 8/1998 | Lewis et al. | |
| 5,789,255 A | 8/1998 | Yu | |
| 5,798,031 A | 8/1998 | Charlton et al. | |
| 5,843,691 A | 12/1998 | Douglas et al. | |
| 5,846,744 A | 12/1998 | Athey et al. | |
| 5,849,174 A | 12/1998 | Sanghera et al. | |
| 5,856,195 A | 1/1999 | Charlton et al. | |
| 5,869,972 A | 2/1999 | Birch et al. | |
| 5,890,489 A | 4/1999 | Elden | |
| 5,904,898 A | 5/1999 | Markart | |
| 5,911,872 A | 6/1999 | Lewis et al. | |
| 5,916,156 A | 6/1999 | Hildenbrand et al. | |
| 5,921,925 A | 7/1999 | Cartmell et al. | |
| 5,945,341 A | 8/1999 | Howard, III | |
| 5,951,836 A | 9/1999 | McAleer et al. | |
| 5,955,179 A | 9/1999 | Kickelhain | |
| 5,956,572 A | 9/1999 | Kidoguchi et al. | |
| 5,965,380 A | 10/1999 | Heller et al. | |
| 5,968,760 A | 10/1999 | Phillips et al. | |
| 5,989,917 A | 11/1999 | McAleer et al. | |
| 5,997,817 A * | 12/1999 | Crismore et al. | 204/403.1 |
| 6,004,441 A | 12/1999 | Fujiwara et al. | |
| 6,036,919 A | 3/2000 | Thym et al. | |
| 6,044,285 A | 3/2000 | Chaiken et al. | |
| 6,071,391 A | 6/2000 | Gotoh et al. | |
| 6,087,182 A | 7/2000 | Jeng et al. | |
| 6,091,975 A | 7/2000 | Daddona et al. | |
| 6,102,872 A | 8/2000 | Doneen et al. | |
| 6,103,033 A * | 8/2000 | Say et al. | 156/73.1 |
| 6,120,676 A | 9/2000 | Heller et al. | |
| 6,121,009 A | 9/2000 | Heller et al. | |
| 6,121,050 A | 9/2000 | Han | |
| 6,129,823 A | 10/2000 | Hughes et al. | |
| 6,134,461 A | 10/2000 | Say et al. | |
| 6,143,164 A | 11/2000 | Heller et al. | |
| 6,144,869 A | 11/2000 | Berner et al. | |
| 6,150,124 A | 11/2000 | Riedel | |
| 6,153,069 A | 11/2000 | Pottgen et al. | |
| RE36,991 E | 12/2000 | Yamamoto et al. | |
| 6,156,173 A | 12/2000 | Gotoh et al. | |
| 6,159,745 A | 12/2000 | Roberts et al. | |
| 6,162,611 A | 12/2000 | Heller et al. | |
| 6,162,639 A | 12/2000 | Douglas | |
| 6,168,957 B1 | 1/2001 | Matzinger et al. | |
| 6,170,318 B1 | 1/2001 | Lewis | |
| 6,174,420 B1 | 1/2001 | Hodges et al. | |
| 6,175,752 B1 | 1/2001 | Say et al. | |

| Patent No. | Date | Inventor |
|---|---|---|
| 6,176,988 B1 | 1/2001 | Kessler |
| 6,179,979 B1 | 1/2001 | Hodges et al. |
| 6,180,062 B1 | 1/2001 | Naka et al. |
| 6,193,873 B1 | 2/2001 | Ohara et al. |
| 6,200,773 B1 | 3/2001 | Ouyang et al. |
| 6,225,078 B1 | 5/2001 | Ikeda et al. |
| 6,241,862 B1 | 6/2001 | McAleer et al. |
| 6,251,260 B1 | 6/2001 | Heller et al. |
| 6,258,229 B1 | 7/2001 | Winarta et al. |
| 6,258,254 B1 | 7/2001 | Miyamoto et al. |
| 6,259,937 B1 | 7/2001 | Schulman et al. |
| 6,268,162 B1 | 7/2001 | Phillips et al. |
| 6,270,637 B1 | 8/2001 | Crismore et al. |
| 6,271,044 B1 | 8/2001 | Ballerstadt et al. |
| 6,277,641 B1 | 8/2001 | Yager |
| 6,281,006 B1 | 8/2001 | Heller et al. |
| 6,284,125 B1 | 9/2001 | Hodges et al. |
| 6,284,550 B1 | 9/2001 | Carroll et al. |
| 6,287,451 B1 | 9/2001 | Winarta et al. |
| 6,287,595 B1 | 9/2001 | Loewy et al. |
| 6,295,506 B1 | 9/2001 | Heinonen et al. |
| 6,299,757 B1 | 10/2001 | Feldman et al. |
| 6,300,123 B1 | 10/2001 | Vadgama et al. |
| 6,300,142 B1 | 10/2001 | Andrewes et al. |
| 6,309,526 B1 | 10/2001 | Fujiwara et al. |
| 6,315,951 B1 | 11/2001 | Markart |
| 6,316,264 B1 | 11/2001 | Corey et al. |
| 6,325,917 B1 | 12/2001 | Maxwell et al. |
| 6,329,161 B1 | 12/2001 | Heller et al. |
| 6,335,203 B1 | 1/2002 | Patel et al. |
| 6,338,790 B1 | 1/2002 | Feldman et al. |
| 6,340,428 B1 | 1/2002 | Ikeda et al. |
| 6,349,230 B1 | 2/2002 | Kawanaka |
| 6,377,894 B1 | 4/2002 | Deweese et al. |
| 6,377,896 B1 | 4/2002 | Sato et al. |
| 6,379,513 B1 | 4/2002 | Chambers et al. |
| 6,395,227 B1 | 5/2002 | Kiser et al. |
| 6,413,395 B1 | 7/2002 | Bhullar et al. |
| 6,413,410 B1 | 7/2002 | Hodges et al. |
| 6,420,128 B1 | 7/2002 | Ouyang et al. |
| 6,444,115 B1 | 9/2002 | Hodges et al. |
| 6,447,657 B1 | 9/2002 | Bhullar et al. |
| 6,454,921 B1 | 9/2002 | Hodges et al. |
| 6,458,258 B2 | 10/2002 | Taniike et al. |
| 6,461,496 B1 | 10/2002 | Feldman et al. |
| 6,475,360 B1 | 11/2002 | Hodges et al. |
| 6,475,372 B1 | 11/2002 | Ohara et al. |
| 6,484,046 B1 | 11/2002 | Say et al. |
| 6,485,923 B1 | 11/2002 | Yani et al. |
| 6,488,827 B1 | 12/2002 | Shartle |
| 6,489,133 B2 | 12/2002 | Phillips et al. |
| 6,491,803 B1 | 12/2002 | Shen et al. |
| 6,491,870 B2 | 12/2002 | Patel et al. |
| 6,501,976 B1 | 12/2002 | Sohrab |
| 6,503,381 B1 | 1/2003 | Gotoh et al. |
| 6,514,718 B2 | 2/2003 | Heller et al. |
| 6,514,769 B2 | 2/2003 | Lee |
| 6,521,110 B1 | 2/2003 | Hodges et al. |
| 6,521,182 B1 | 2/2003 | Shartle et al. |
| 6,525,330 B2 | 2/2003 | Paolini et al. |
| 6,525,549 B1 | 2/2003 | Poellmann |
| 6,526,298 B1 | 2/2003 | Khalil et al. |
| 6,531,040 B2 | 3/2003 | Musho et al. |
| 6,531,322 B1 | 3/2003 | Jurik et al. |
| 6,540,890 B1 | 4/2003 | Bhullar et al. |
| 6,540,891 B1 | 4/2003 | Stewart et al. |
| 6,541,266 B2 | 4/2003 | Modzelewski et al. |
| 6,544,474 B2 | 4/2003 | Douglas |
| 6,549,796 B2 | 4/2003 | Schrab |
| 6,551,494 B1 | 4/2003 | Heller et al. |
| 6,555,061 B1 | 4/2003 | Leong et al. |
| 6,558,528 B1 | 5/2003 | Matzinger |
| 6,560,471 B1 | 5/2003 | Heller et al. |
| 6,561,989 B2 | 5/2003 | Whitson |
| 6,565,509 B1 | 5/2003 | Say et al. |
| 6,565,738 B1 | 5/2003 | Henning et al. |
| 6,571,651 B1 | 6/2003 | Hodges |
| 6,572,822 B2 | 6/2003 | Jurik et al. |
| 6,576,101 B1 | 6/2003 | Heller et al. |
| 6,576,117 B1 | 6/2003 | Iketaki et al. |
| 6,576,416 B2 | 6/2003 | Haviland et al. |
| 6,576,461 B2 | 6/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,594,514 B2 | 7/2003 | Berner et al. |
| 6,599,406 B1 | 7/2003 | Kawanaka et al. |
| 6,599,407 B2 | 7/2003 | Taniike et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,603 B2 | 9/2003 | Yaralli et al. |
| 6,618,934 B1 | 9/2003 | Feldman et al. |
| 6,627,057 B1 | 9/2003 | Bhullar et al. |
| 6,632,349 B1 | 10/2003 | Hodges et al. |
| 6,638,415 B1 | 10/2003 | Hodges et al. |
| 6,638,716 B2 | 10/2003 | Heller et al. |
| 6,645,359 B1 * | 11/2003 | Bhullar et al. ........... 204/403.01 |
| 6,654,625 B1 | 11/2003 | Say et al. |
| 6,656,702 B1 | 12/2003 | Yugawa et al. |
| 6,662,439 B1 * | 12/2003 | Bhullar .......................... 29/825 |
| 6,676,995 B2 | 1/2004 | Dick et al. |
| 6,689,411 B2 | 2/2004 | Dick et al. |
| 6,716,620 B2 | 4/2004 | Bashir et al. |
| 6,719,887 B2 | 4/2004 | Hasegawa et al. |
| 6,723,371 B2 | 4/2004 | Chih-Lui |
| 6,746,582 B2 | 6/2004 | Heller et al. |
| 6,749,740 B2 | 6/2004 | Liamos et al. |
| 6,764,581 B1 | 7/2004 | Forrow et al. |
| 6,767,440 B1 * | 7/2004 | Bhullar et al. ........... 204/403.01 |
| 6,776,888 B2 | 8/2004 | Yamamoto et al. |
| 6,777,243 B2 | 8/2004 | Fukuoka et al. |
| 6,787,013 B2 | 9/2004 | Chang et al. |
| 6,800,488 B2 | 10/2004 | Khan et al. |
| 6,814,844 B2 | 11/2004 | Bhullar et al. |
| 6,818,180 B2 | 11/2004 | Douglas |
| 6,821,483 B2 | 11/2004 | Phillips et al. |
| 6,827,829 B2 | 12/2004 | Kawanaka et al. |
| 6,830,669 B2 | 12/2004 | Miyazaki et al. |
| 6,833,110 B2 | 12/2004 | Black |
| 6,841,389 B2 | 1/2005 | Novikov et al. |
| 6,856,125 B2 | 2/2005 | Kermani |
| 6,860,978 B2 | 3/2005 | Yamanishi et al. |
| 6,863,800 B2 | 3/2005 | Karinka |
| 6,881,322 B2 | 4/2005 | Tokunaga et al. |
| 6,881,550 B2 | 4/2005 | Phillips et al. |
| 6,881,551 B2 | 4/2005 | Heller |
| 7,041,206 B2 | 5/2006 | Gephart et al. |
| 7,073,246 B2 * | 7/2006 | Bhullar et al. .................. 29/595 |
| 7,276,146 B2 * | 10/2007 | Wilsey .......................... 205/792 |
| 8,287,703 B2 * | 10/2012 | Bhullar et al. ........... 204/403.01 |
| 2001/0042683 A1 | 11/2001 | Musho et al. |
| 2001/0052470 A1 | 12/2001 | Hodges et al. |
| 2001/0053535 A1 | 12/2001 | Bashir et al. |
| 2001/0054319 A1 | 12/2001 | Heller et al. |
| 2001/0055784 A1 | 12/2001 | Noda et al. |
| 2002/0004196 A1 | 1/2002 | Whitson |
| 2002/0019707 A1 | 2/2002 | Cohen et al. |
| 2002/0043471 A1 | 4/2002 | Ikeda et al. |
| 2002/0044890 A1 | 4/2002 | Black |
| 2002/0053523 A1 | 5/2002 | Liamos et al. |
| 2002/0081588 A1 | 6/2002 | De Lumley-woodyear et al. |
| 2002/0082797 A1 | 6/2002 | Deweese et al. |
| 2002/0084196 A1 | 7/2002 | Liamos et al. |
| 2002/0092612 A1 | 7/2002 | Davies et al. |
| 2002/0100685 A1 | 8/2002 | Huang et al. |
| 2002/0102739 A1 | 8/2002 | Nomura et al. |
| 2002/0112969 A1 | 8/2002 | Hodges et al. |
| 2002/0125145 A1 | 9/2002 | Ohara et al. |
| 2002/0133064 A1 | 9/2002 | Ueno et al. |
| 2002/0137200 A1 | 9/2002 | Takahashi et al. |
| 2002/0137230 A1 | 9/2002 | Nadaoka et al. |
| 2002/0139692 A1 | 10/2002 | Tokunaga et al. |
| 2002/0148739 A2 | 10/2002 | Liamos et al. |
| 2002/0157948 A2 | 10/2002 | Liamos et al. |
| 2002/0164822 A1 | 11/2002 | Takahashi et al. |

| Publication No. | Date | Inventor |
|---|---|---|
| 2002/0168290 A1 | 11/2002 | Yuzhakov et al. |
| 2002/0175087 A1 | 11/2002 | Hodges et al. |
| 2002/0177788 A1 | 11/2002 | Hodges et al. |
| 2002/0179440 A1 | 12/2002 | Tokunaga et al. |
| 2002/0179442 A1 | 12/2002 | Miyazaki et al. |
| 2002/0185385 A1 | 12/2002 | Charlton |
| 2002/0189941 A1 | 12/2002 | Katsuki |
| 2003/0000834 A1 | 1/2003 | Yoshioka et al. |
| 2003/0024811 A1 | 2/2003 | Davies et al. |
| 2003/0032875 A1 | 2/2003 | Taniike et al. |
| 2003/0042137 A1 | 3/2003 | Mao et al. |
| 2003/0042150 A1 | 3/2003 | Ryu et al. |
| 2003/0046811 A1 | 3/2003 | Chang et al. |
| 2003/0073152 A1 | 4/2003 | Phillips et al. |
| 2003/0073153 A1 | 4/2003 | Phillips et al. |
| 2003/0088166 A1 | 5/2003 | Say et al. |
| 2003/0094383 A1 | 5/2003 | Kermani |
| 2003/0097981 A1 | 5/2003 | Dick et al. |
| 2003/0098233 A1 | 5/2003 | Kermani et al. |
| 2003/0099773 A1 | 5/2003 | Dick et al. |
| 2003/0100030 A1 | 5/2003 | Nadaoka et al. |
| 2003/0102213 A1 | 6/2003 | Gotoh et al. |
| 2003/0106809 A1 | 6/2003 | Kermani et al. |
| 2003/0109798 A1 | 6/2003 | Kermani |
| 2003/0132110 A1 | 7/2003 | Hasegawa et al. |
| 2003/0143113 A2 | 7/2003 | Yuzhakov et al. |
| 2003/0146110 A1 | 8/2003 | Karinka et al. |
| 2003/0150724 A1 | 8/2003 | Kawanaka et al. |
| 2003/0155237 A1 | 8/2003 | Surridge et al. |
| 2003/0159944 A1 | 8/2003 | Pottgen et al. |
| 2003/0159945 A1 | 8/2003 | Miyazaki et al. |
| 2003/0164293 A1 | 9/2003 | Hodges et al. |
| 2003/0175841 A1 | 9/2003 | Watanabe et al. |
| 2003/0175946 A1 | 9/2003 | Tokunaga et al. |
| 2003/0176183 A1 | 9/2003 | Drucker et al. |
| 2003/0180183 A1 | 9/2003 | Fukuoka et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199893 A1 | 10/2003 | Boecker et al. |
| 2003/0201194 A1 | 10/2003 | Heller et al. |
| 2003/0203498 A1 | 10/2003 | Neel et al. |
| 2003/0203503 A1 | 10/2003 | Fukuoka et al. |
| 2003/0217918 A1 | 11/2003 | Davies et al. |
| 2004/0005721 A1 | 1/2004 | Tanike et al. |
| 2004/0016642 A1 | 1/2004 | Miyazaki et al. |
| 2004/0020777 A1 | 2/2004 | Miyamoto et al. |
| 2004/0067166 A1 | 4/2004 | Karinka et al. |
| 2004/0094432 A1 | 5/2004 | Neel et al. |
| 2004/0094433 A1 | 5/2004 | Neel et al. |
| 2004/0096928 A1 | 5/2004 | Hasegawa et al. |
| 2004/0099540 A1 | 5/2004 | Neel et al. |
| 2004/0104131 A1 | 6/2004 | Neel et al. |
| 2004/0106941 A1 | 6/2004 | Roe et al. |
| 2004/0127818 A1 | 7/2004 | Roe et al. |
| 2004/0127819 A1 | 7/2004 | Roe |
| 2004/0182703 A1 | 9/2004 | Bell et al. |
| 2004/0206625 A1 | 10/2004 | Bhullar et al. |
| 2004/0251131 A1 | 12/2004 | Ueno et al. |
| 2005/0008537 A1 | 1/2005 | Mosoiu et al. |
| 2005/0013731 A1 | 1/2005 | Burke et al. |
| 2005/0016844 A1 | 1/2005 | Burke et al. |
| 2005/0019212 A1 | 1/2005 | Bhullar et al. |

FOREIGN PATENT DOCUMENTS

| | | |
|---|---|---|
| DE | 3922478 A1 | 1/1991 |
| DE | 199 51 721 A1 | 6/2000 |
| DE | 102 22 428 A | 12/2002 |
| DE | 102 22 428 A1 | 12/2002 |
| EP | 0 057 110 B2 | 8/1982 |
| EP | 0 127 958 B2 | 12/1984 |
| EP | 0 034 049 B1 | 1/1985 |
| EP | 0 164 180 B2 | 12/1985 |
| EP | 0 170 375 A2 | 2/1986 |
| EP | 0 171 148 B1 | 2/1986 |
| EP | 0 359 831 B1 | 7/1986 |
| EP | 0 230 472 B2 | 8/1987 |
| EP | 0 255 291 B1 | 2/1988 |
| EP | 0 267 724 A | 5/1988 |
| EP | 0 267 724 A1 | 5/1988 |
| EP | 0 287 883 A1 | 10/1988 |
| EP | 0 359 831 B1 | 3/1990 |
| EP | 0 383 322 B1 | 8/1990 |
| EP | 0 438 344 B1 | 7/1991 |
| EP | 0 471 986 A | 2/1992 |
| EP | 0 471 986 A2 | 2/1992 |
| EP | 0 480 703 A2 | 4/1992 |
| EP | 0 537 761 A2 | 4/1993 |
| EP | 0 546 536 B1 | 7/1993 |
| EP | 0 732 406 A1 | 9/1996 |
| EP | 0 736 607 A1 | 10/1996 |
| EP | 0 740 786 B1 | 11/1996 |
| EP | 0 480 703 B1 | 3/1997 |
| EP | 0 837 320 A3 | 4/1998 |
| EP | 0 840 122 A2 | 5/1998 |
| EP | 0 851 224 B1 | 7/1998 |
| EP | 0 873 514 B1 | 10/1998 |
| EP | 0 876 506 B1 | 11/1998 |
| EP | 0 882 226 B1 | 12/1998 |
| EP | 0 887 421 A1 | 12/1998 |
| EP | 0 958 495 B1 | 11/1999 |
| EP | 0 964 059 A2 | 12/1999 |
| EP | 0 967 480 B1 | 12/1999 |
| EP | 0 987 544 A1 | 3/2000 |
| EP | 1 009 850 B1 | 6/2000 |
| EP | 1 024 358 A1 | 8/2000 |
| EP | 1 074 832 A1 | 2/2001 |
| EP | 1 098 000 A2 | 5/2001 |
| EP | 1 098 000 A3 | 5/2001 |
| EP | 1 102 991 B1 | 5/2001 |
| EP | 1 119 637 B1 | 8/2001 |
| EP | 1 129 211 B1 | 9/2001 |
| EP | 1 130 390 A1 | 9/2001 |
| EP | 1 203 956 A2 | 10/2001 |
| EP | 1 152 239 A1 | 11/2001 |
| EP | 1 156 324 A1 | 11/2001 |
| EP | 1203956 * | 5/2002 |
| EP | 1 225 448 A2 | 7/2002 |
| EP | 1 235 069 A1 | 8/2002 |
| EP | 1 236 995 A1 | 9/2002 |
| EP | 1 256 798 A1 | 11/2002 |
| EP | 1 260 589 A2 | 11/2002 |
| EP | 1 275 732 A1 | 1/2003 |
| EP | 1 281 955 A1 | 2/2003 |
| EP | 1 288 654 A1 | 3/2003 |
| EP | 1 308 720 A1 | 5/2003 |
| EP | 1 312 919 A2 | 5/2003 |
| EP | 1 316 367 A | 6/2003 |
| EP | 1 316 367 A | 6/2003 |
| EP | 1 318 396 A1 | 6/2003 |
| EP | 1 324 025 A2 | 7/2003 |
| EP | 1 324 038 A2 | 7/2003 |
| EP | 1 327 881 A1 | 7/2003 |
| EP | 1 352 611 A1 | 10/2003 |
| EP | 1 352 969 A1 | 12/2003 |
| EP | 1 369 684 A1 | 12/2003 |
| EP | 1 369 687 A1 | 12/2003 |
| EP | 1 391 716 A2 | 2/2004 |
| EP | 1 394 535 A1 | 3/2004 |
| EP | 1 431 758 A | 6/2004 |
| EP | 1 431 758 A1 | 6/2004 |
| GB | 2365123 A | 2/2002 |
| JP | 63128252 A2 | 5/1988 |
| JP | 1291153 A2 | 11/1989 |
| JP | 05-312761 | 11/1993 |
| JP | 05-315703 | 11/1993 |
| JP | H07-66499 U | 3/1995 |
| JP | 07-290751 | 11/1995 |
| JP | 09-189675 | 7/1997 |
| JP | 09-260697 | 10/1997 |
| JP | 10-052780 | 2/1998 |
| JP | 10-241992 | 9/1998 |
| JP | 10-275959 | 10/1998 |
| JP | 10-303444 | 11/1998 |
| JP | 10 307119 A | 11/1998 |
| JP | 11 337514 A | 12/1999 |
| JP | 2003/511851 | 3/2003 |
| JP | 2003-511851 | 3/2003 |

| | | |
|---|---|---|
| JP | 2004-20465 | 1/2004 |
| WO | WO 86/07632 | 12/1986 |
| WO | WO 89/09397 | 10/1989 |
| WO | WO 91/02391 A1 | 2/1991 |
| WO | WO 92/22669 | 12/1992 |
| WO | WO 94/16095 | 7/1994 |
| WO | WO 94/28414 | 12/1994 |
| WO | WO 94/29705 | 12/1994 |
| WO | WO 95/22597 | 8/1995 |
| WO | WO 95/22881 A1 | 8/1995 |
| WO | WO 96/07908 | 3/1996 |
| WO | WO 96/15454 | 5/1996 |
| WO | WO 96/33403 | 10/1996 |
| WO | WO 97/02487 | 1/1997 |
| WO | WO 97/29847 | 8/1997 |
| WO | WO 97/30344 | 8/1997 |
| WO | WO 97/34140 A | 9/1997 |
| WO | WO 97/34140 A1 | 9/1997 |
| WO | WO 97/39343 | 10/1997 |
| WO | WO 97/45719 | 12/1997 |
| WO | WO 98/30904 A1 | 7/1998 |
| WO | WO 98/35225 | 8/1998 |
| WO | WO 01/25775 A1 | 11/1998 |
| WO | WO 98/55853 | 12/1998 |
| WO | WO 98/55856 A1 | 12/1998 |
| WO | WO 99/05516 | 2/1999 |
| WO | WO 99/13099 | 3/1999 |
| WO | WO 99/13100 | 3/1999 |
| WO | WO 99/13101 A1 | 3/1999 |
| WO | WO 99/19507 * | 4/1999 |
| WO | WO 99/30152 | 6/1999 |
| WO | WO 99/32881 | 7/1999 |
| WO | WO 99/39627 | 8/1999 |
| WO | WO 99/45387 | 9/1999 |
| WO | WO 99/51974 | 10/1999 |
| WO | WO 99/58709 | 11/1999 |
| WO | WO 99/64620 | 12/1999 |
| WO | WO 00/10007 | 2/2000 |
| WO | WO 00/18294 A1 | 4/2000 |
| WO | WO 00/20626 | 4/2000 |
| WO | WO 00/26638 | 5/2000 |
| WO | WO 00/28068 | 5/2000 |
| WO | WO 00/33063 A | 6/2000 |
| WO | WO 00/33063 A1 | 6/2000 |
| WO | WO 00/33072 | 6/2000 |
| WO | WO 00/33074 | 6/2000 |
| WO | WO 00/42422 | 7/2000 |
| WO | WO 00/60340 | 10/2000 |
| WO | WO 00/62047 | 10/2000 |
| WO | WO 00/73778 A1 | 12/2000 |
| WO | WO 00/73785 A2 | 12/2000 |
| WO | WO 00/78992 A2 | 12/2000 |
| WO | WO 01/25775 A1 | 4/2001 |
| WO | WO 01/25776 A1 | 4/2001 |
| WO | WO 01/33216 A1 | 5/2001 |
| WO | WO 01/36953 A1 | 5/2001 |
| WO | WO 01/40788 A1 | 6/2001 |
| WO | WO 01/46457 A2 | 6/2001 |
| WO | WO 01/57238 A2 | 8/2001 |
| WO | WO 01/57239 A2 | 8/2001 |
| WO | WO 01/57510 A2 | 8/2001 |
| WO | WO 01/67099 A1 | 9/2001 |
| WO | WO 01/71328 A1 | 9/2001 |
| WO | WO 01/71329 A1 | 9/2001 |
| WO | WO 01/72220 A1 | 10/2001 |
| WO | WO 01/73109 A2 | 10/2001 |
| WO | WO 01/73114 A2 | 10/2001 |
| WO | WO 01/73124 A2 | 10/2001 |
| WO | WO 01/73419 A1 | 10/2001 |
| WO | WO 01/73420 A1 | 10/2001 |
| WO | WO 01/75438 A2 | 10/2001 |
| WO | WO 01/84133 A1 | 11/2001 |
| WO | WO 02/00112 A2 | 1/2002 |
| WO | WO 02/08750 A1 | 1/2002 |
| WO | WO 02/08753 A2 | 1/2002 |
| WO | WO 02/10728 A1 | 2/2002 |
| WO | WO 02/14535 A2 | 2/2002 |
| WO | WO 02/22855 A2 | 3/2002 |
| WO | WO 02/32559 A1 | 4/2002 |
| WO | WO 02/49507 A1 | 6/2002 |
| WO | WO 02/50609 | 6/2002 |
| WO | WO 02/054055 A1 | 7/2002 |
| WO | WO 02/057767 A1 | 7/2002 |
| WO | WO 02/057768 A1 | 7/2002 |
| WO | WO 02/057781 A2 | 7/2002 |
| WO | WO 02/058537 A2 | 8/2002 |
| WO | WO 02/067768 A2 | 9/2002 |
| WO | WO 02/070734 A1 | 9/2002 |
| WO | WO 02/071044 A1 | 9/2002 |
| WO | WO 02/078512 A2 | 10/2002 |
| WO | WO 02/078533 A2 | 10/2002 |
| WO | WO 02/086483 A1 | 10/2002 |
| WO | WO 02/097418 A1 | 12/2002 |
| WO | WO 02/103343 A1 | 12/2002 |
| WO | WO 03/005015 A1 | 1/2003 |
| WO | WO 03/012422 A1 | 2/2003 |
| WO | WO 03/014740 A1 | 2/2003 |
| WO | WO 03/014741 A1 | 2/2003 |
| WO | WO 03/029804 A1 | 4/2003 |
| WO | WO 03/032411 A2 | 4/2003 |
| WO | WO 03/042679 A1 | 5/2003 |
| WO | WO 03/042680 A1 | 5/2003 |
| WO | WO 03/043945 A1 | 5/2003 |
| WO | WO 03/044511 A2 | 5/2003 |
| WO | WO 03/048756 A1 | 6/2003 |
| WO | WO 03/060154 A2 | 7/2003 |
| WO | WO 03/067252 A2 | 8/2003 |
| WO | WO 03/069304 A2 | 8/2003 |
| WO | WO 03/083469 A2 | 10/2003 |
| WO | WO 03/085372 A2 | 10/2003 |
| WO | WO 03/091717 A1 | 11/2003 |
| WO | WO 2004/005908 A1 | 1/2004 |
| WO | WO 2004/011394 A1 | 5/2004 |
| WO | WO 2004/113901 A1 | 12/2004 |
| WO | WO 2004/113902 A1 | 12/2004 |
| WO | WO 2004/113914 A1 | 12/2004 |

OTHER PUBLICATIONS

Richard F. Taylor et al., "An Acetylcholine Receptor-Based Biosensor for the Detection of Cholinergic Agents", Analytica Chimica Acta, 1988, pp. 131-138.
T. Boltshauser et al., "Capacitive Humidity Sensors in SACMOS Technology with Moisture Absorbing Photosensitive Polyimide", Sensors and Actuators, 1991, pp. 509-512.
Tsutomu Horiuchi et al., "Limiting Current Enhancement by Self-Induced Redox Cycling on a Micro-Macro Twin Electrode", Journal of the Electrochemical Society, Dec. 1991, pp. 3549-3553, vol. 138, No. 12.
Vasile V. Cosofret et al., "Microfabricated Sensor Arrays Sensitive to pH and K+ for Ionic Distribution Measurements in the Beating Heart", Analytical Chemistry, May 15, 1995, pp. 1647-1653, vol. 67, No. 10.
W. Preidel et al., "In vitro measurements with electrocatalytic glucose sensor in blood", Biomed. Biochem. Acta, 1989, pp. 897-903.
Written Opinion from Intellectual Property Office of Singapore.
Koichi Aoki, "Quantitative analysis of reversible diffusion-controlled currents of redox soluble species at interdigitated array electrodes under steady-state conditions", Journal of Electroanalytical Chemistry, pp. 269-282, issue/volume vol. 256, No. 2, Elsevier Sequoia S.A., Lausanne.
"Verarbeitung von Dispersionshaftlebstoffen", 1022 Adhasion, 37 Dec. 1993, No. 12, Muchen, DE.
Brian A. Gregg et al., "Cross-Linked Redox Gels Containing Glucose Oxidase for Amperometric Biosensor Applications", Analytical Chemistry, Feb. 1, 1990, pp. 258-263, vol. 62, No. 3.
Cosimino Malitesta et al., "Glucose Fast-Response Amperometric Sensor Based on Glucose Oxidase Immobilized in an Electropolymerized Poly (o-phenylenediamine) Film", Analytical Chemistry, Dec. 15, 1990, pp. 2735-2740, vol. 62, No. 24.
D.J. Meier et al., "Laser Direct Patterning Mass-Produces Microstructures", Europhotonics, Nov. 2001, vol. 6, No. 6, pp. 25-27.
D.J. Meier et al., "Laser Structuring of Fine Lines", Circuitree, Sep. 2000, vol. 13, pp. 36-42.

David L. Williams et al., "Electrochemical-Enzymatic Analysis of Blood Glucose and Lactate", Analytical Chemistry, Jan. 1970, pp. 118-121, vol. 42, No. 1.

Koichi Aoki, "Theory of the steady-state current of a redox couple at interdigitated array electrodes of which pairs are insulated electrically by steps", Journal of Electroanalytical Chemistry, Oct. 10, 1989, pp. 35-41, vol. 270.

Leonard M. Tender et al.,"Electrochemical Patterning of Self-Assembled Monolayers onto Microscopic Arrays of Gold Electrodes Fabricated by Laser Ablation", Langmuir, pp. 5515-5518 (1996), vol. 12, No. 23.

M. Beyer et al., "Development and application of a new enzyme sensor type based on the EIS-capacitance structure for bioprocess control", Biosensors & Bioelectronics, 1994, pp. 17-21.

Matsuhiko Nishizawa et al., "Penicillin Sensor Based on a Microarray Electrode Coated with pH-responsive Polypyrrole", Analytical Chemistry, Nov. 1, 1992, pp. 2642-2644, vol. 64, No. 21.

N.A. Morris et al., "An Electrochemical Capillary Fill Device for the Analysis of Glucose Incorporating Glucose Oxidase and Ruthenium (III) Hexamine as Mediator", Electroanalysis, 1992, pp. 1-9, vol. 4.

Colon, Will, "Microanalysis: Biosensors at the Point of Care", MST News, pp. 9-11 (Jan. 2005).

DE 39 922 478 A1 Translation 2009.

Duley, W. W., "UV Lasers: effects and applications in materials science", Cambridge University Press, pp. 78-97 1996.

Erol C. Harvey et al., "Fabrication Techniques and Their Applications to Produce Novel Micromachined Structures and Devices Using Excimer Laser Projection", Exitech Ltd., Hanborough Park, Long Hanborough, Oxford, UK, SPIE vol. 3223, 1997.

European Patent Application 0 438 344 published Jul. 24, 1991 English Language Abstract.

Japanese Patent Publication 05-315703 published Nov. 26, 1993 English Language Abstract.

Japanese Patent Publication 07-290751 published Nov. 7, 1995 English Language Abstract.

Japanese Patent Publication 09-260697 published Oct. 3, 1997 English Language Abstract.

Japanese Patent Publication 10-052780 published Feb. 24, 1998 English Language Abstract.

Japanese Patent Publication 10-241992 published Sep. 11, 1998 English Language Abstract.

Japanese Patent Publication 10-275959 published Oct. 13, 1998 English Language Abstract.

Japanese Patent Publication 10-303444 published Nov. 13, 1998 English Language Abstract.

Koichi Aoki, "Quantitative analysis of reversible diffusion-controlled currents of redox soluble species at interdigitated array electrodes under steady-state conditions", Journal of Electroanalytical Chemistry, pp. 269-282, issue/volume vol. 256, No. 2, Elesevier Sequoia S.A., Lausanne 1988.

Nadeem H. Rizvi et al., "An Excimer Laser Micromachining System for the Production of BioParticle Electromanipulation Devices", Exitech Ltd., Hanborough Park, Oxford and Institute of Molecular and Biomolecular Electronics, University of Wales, Bangor, SPIE vol. 3224 (1997)

Nadeem H. Rizvi et al., "Direct Manufacture of Miniature Bio-Particle Electro-Manipulator Devices Using Excimer Laser Mask Projection Techniques", Exitech Ltd., and University of Wales, UK (Aug. 12, 1998).

Sheppard, Jr., Norman F., "Electrical Conductivity Measurements Using Microfabricated Interdigitated Electrodes", Anal. Chem., 1993, 85, pp. 1199-1202.

Srinivasan, R., "Ablation of Polymers and Biological Tissue by Ultraviolet Lasers", Science, vol. 234, pp. 559-564 (Oct. 21, 1986).

Srinivasan, R., "Ultraviolet Laser Ablation of Organic Polymers", Chem. Rev. 1989, 89, pp. 1303-1316.

Tahhan, Isam, "Biocompatible Microstructuring of Polymers and Electrodes with an Excimer Laser", MEDICS Workshop 2000 Speakers Abstracts 2000.

Wu, Jeff C. et al., "Single-shot Excimer Laser Ablation of Thick Polymer Resists on Metallic Substrates", AMP Journal of Technology, vol. 1, pp. 69-79 (Nov. 1991).

Zongyl, Qin et al., "Excimer laser patterning on thin polymer surfaces for electrochemical gas sensors", Proceedings of the International Conference on Lasers (1999).

* cited by examiner

BIOSENSOR AND METHOD OF MAKING

CROSS-REFERENCE TO RELATED APPLICATIONS

This application is a divisional of U.S. patent application Ser. No. 10/871,937, filed Jun. 18, 2004, now abandoned; which is a continuation-in-part of U.S. patent application Ser. No. 10/601,144 filed Jun. 20, 2003, now U.S. Pat. No. 7,073,246; a continuation-in-part of U.S. application Ser. No. 10/264,891 filed Oct. 4, 2002, now U.S. Pat. No. 7,276,146; a continuation-in-part of U.S. application Ser. No. 09/840,843 filed Apr. 24, 2001, now U.S. Pat. No. 6,767,440; a continuation-in-part of U.S. application Ser. No. 09/684,257 filed Oct. 6, 2000, now U.S. Pat. No. 6,645,359; and a continuation-in-part of U.S. application Ser. No. 09/411,940 filed Oct. 4, 1999, now U.S. Pat. No. 6,662,439, each of which is hereby incorporated by reference in its entirety.

FIELD OF THE INVENTION

The present invention relates to a method of making a biosensor, more specifically a biosensor having electrode sets formed by laser ablation.

BACKGROUND

Electrochemical biosensors are well known and have been used to determine the concentration of various analytes from biological samples, particularly from blood. Examples of such electrochemical biosensors are described in U.S. Pat. Nos. 5,413,690; 5,762,770; 5,798,031; and 6,129,823 each of which is hereby incorporated by reference.

It is desirable for electrochemical biosensors to be able to analyze analytes using as small a sample as possible, and it is therefore necessary to minimize the size of their parts, including the electrodes, as much as possible. As discussed below, screen-printing, laser scribing, and photolithography techniques have been used to form miniaturized electrodes.

Electrodes formed by screen-printing techniques are formed from compositions that are both electrically conductive and screen-printable. Furthermore, screen printing is a wet chemical technique that generally allows reliable formation of structures and patterns having a gap width or feature size of approximately 75 µm or greater. Such techniques are well known to those of ordinary skill in the art.

Laser scribing is a technique that usually uses a high power excimer laser, such as a krypton-fluoride excimer laser with an illumination wavelength of 248 nm, to etch or scribe individual lines in the conductive surface material and to provide insulating gaps between residual conductive material which forms electrodes and other desired components. This scribing is accomplished by moving the laser beam across the surface to be ablated. The scribing beam generally has a relatively small, focused size and shape, which is smaller than the features desired for the product, and the formation of the product therefore requires rastering techniques. Such a technique can be rather time consuming if a complex electrode pattern is to be formed on the surface. Further, the precision of the resulting edge is rather limited. This scribing technique has been used to ablate metals, polymers, and biological material. Such systems are well known to those of ordinary skill in the art, and are described in U.S. Pat. Nos. 5,287,451, 6,004,441, 6,258,229, 6,309,526, WO 00/73785, WO 00/73788, WO 01/36953, WO 01/75438, and EP 1 152 239 each of which is hereby incorporated by reference. It would be desirable to have a new method of forming electrodes which allows precise electrode edges, a variety of feature sizes, and which can be formed in a high speed/throughput fashion without the use of rastering.

SUMMARY OF THE INVENTION

The present invention provides an electrochemical biosensor with electrode elements that possess smooth, high-quality edges. These smooth edges define gaps between electrodes, electrode traces and contact pads. Due to the remarkable edge smoothness achieved with the present invention, the gaps can be quite small, the advantages of which are described below. Further, the present invention provides a novel biosensor production method in which entire electrode patterns for the inventive biosensors can be formed all at one, in nanoseconds—irrespective of the complexity of the electrode patterns or the amount of conductive material that must be ablated to form them.

In one form thereof, the present invention provides a biosensor comprising a base substrate having first and second electrode elements formed thereon. The first and second electrode elements have first and second respective edges defining a gap therebetween. The gap has a width and a length. The first edge is spaced by a first distance from a first "theoretical line" that corresponds to the desired or ideal shape and location of the first edge. This first distance varies along the length of the gap because the edge actually produced is not as smooth or perfect as the desired theoretical line. The standard deviation of the first distance is less than about 6 µm over the entire length of the gap. The biosensor also includes a reagent at least partially covering the base substrate and one or more layers overlying and adhered to the base substrate. The one or more layers cooperate to form a sample-receiving chamber and a cover for the biosensor, and at least a portion of both the reagent and an electrode are positioned in the chamber.

In a related form of the inventive biosensor described above, the actual or real deviation of the edge from the theoretical line is no more than about 6 µm along the entire length of the gap. Stated another way, the distance between the edge actually produced and the theoretical line (if the edge were perfect) is less than 6 µm no matter where along the gap the distance is measured. More preferably, the real deviation is less than about 4 µm, most preferably less than about 2 µm. In this most preferred form, it is possible to space the electrodes as close as about 5 µm without having the electrical components touch and thus short. Similarly, the width of the features of the electrical pattern such as electrode fingers or traces can be as narrow as about 10 µm. As discussed in detail below, the close spacing of electrode components allowed by the present invention in turn allows a greater number of electrode elements and thus greater functionality in a smaller area.

The smoothness or quality of the edges is most important in areas of the biosensor where adjacent edges are positioned close to one another, e.g., the gap between two electrodes. In a preferred aspect of the present invention, like the first edge discussed above, the second edge is spaced from a second theoretical line by a second distance that varies along the length of the gap. The first and the second theoretical lines thus define a "theoretical gap" therebetween. If the production process were perfect, and if the edges were intended to be straight and parallel to one another, the theoretical gap width would be constant along its length. In practice, however, the actual gap width varies from the theoretical one along the length of the gap. Deviations from theoretical of the first and second edges can be compounded to produce larger variations in the actual gap width than are produced in either edge alone. In a preferred form of the invention, the standard deviation of the second distance is less than about 6 µm over the entire length of the gap. More preferably, the standard deviation of both the first and second distances is less than about 2 µm, even more preferably, less than about 1 µm.

In another preferred form of the invention, the method comprises removing at least 10% of the conductive material, more preferably at least 50% of the conductive material, and most preferably at least 90% of the conductive material. The conductive material is preferably removed by broad field laser ablation, which allows relatively large percentages of the conductive layer to be removed from the base substrate very quickly to form electrode patterns. For example, in preferred forms, the entire electrode pattern for a biosensor is formed by broad field laser ablation in less than about 0.25 seconds, more preferably in less than about 50 nanoseconds, and most preferably in less than about 25 nanoseconds.

As noted above, the inventive method also allows for the placement of two or more electrode sets having different feature sizes in the same biosensor. Furthermore, as noted above, the feature sizes can be quite small and spaced close together.

In another form, the present invention provides an efficient and fast method for mass producing biosensors having electrode patterns with the highly desirable smooth edges discussed above. In this method, a web of base substrate material having a metal conductive layer formed thereon is provided. An image of an electrode pattern is projected onto the metal conductive layer with a laser apparatus such that an electrode pattern that corresponds to the image is formed by laser ablation on the web of base substrate material. Either the laser apparatus or the web of base substrate material (or both) is moved and this process is repeated to produce many electrode patterns at spaced intervals along the web of base substrate material. A reagent is deposited on the web of base substrate material and at least partially covers each electrode pattern of the plurality of electrode patterns. At least one web of a covering layer or a spacing layer is laminated over the web of base substrate material, thereby forming a cover and a sample-receiving cavity for each biosensor. The resulting laminated web of layers is then cut into individual biosensors.

In a preferred form, the image projected by the laser apparatus is of the complete electrode pattern for one of the biosensors, such that the complete electrode pattern for each biosensor is formed in a single step with a single laser image. In another preferred form, more than one entire electrode pattern is formed all at once; i.e., the image includes patterns for two or more biosensors.

In another preferred form, the electrode pattern includes at least two electrode sets having different feature sizes. Examples of this may include one set of electrodes for measuring analyte concentration and another set for detecting whether and when the biosensor has received an adequate dose of sample fluid. The inventive biosensor may also include electrode elements providing other features, such as biosensor identification, calibration or other information associated with the biosensor.

One advantage of this inventive mass production process is that it is much faster than prior art processes that require forming electrode patterns by screen printing, lithography, rastering and the like. With the laser ablation process employed by the present invention, the entire electrode pattern for a biosensor can be formed all at once, in a single step, in only nanoseconds. This allows a continuous web of material from which the individual biosensors will ultimately be cut to be processed at speeds of 60 meters per minute or greater.

Not only is the inventive process much faster than prior art processes, it provides biosensors with electrode patterns whose edges have much better edge quality than prior art biosensors. Edge quality becomes increasingly important as electrode spacing becomes closer. Close electrode spacing is desirable because it generally increases the accuracy of the test result, reduces sample size, and yields a quicker test. Additionally, it allows a greater quantity of electrode elements and associated functionalities to be packed into a single biosensor.

Yet another advantage of the inventive production method is that it allows a large percentage of the electrically conductive layer to be removed from the base substrate all at once. By contrast, prior art rastering processes use a collimated laser beam that slowly scribes and removes only a thin line of conductive material, which is a much longer and less versatile process in comparison with the present invention.

Another advantage related to the one just noted is that the manufacturing process of the present invention provides great freedom in the shape and variation in the electrode pattern produced in the inventive biosensors. Asymmetric or anisotropic electrode patterns do not present a problem with the manufacturing process of the present invention. Further, since the electrode pattern is preferably projected on the base substrate by a laser image formed by a mask, limitations as to size, shape, number of electrode patterns, gap width, etc. that are encountered with prior art processes are reduced. By comparison, rastering processes are typically limited to movement of a focused laser beam along axes that are oriented 90 degrees relative to one another. The resulting patterns typically are limited to thin lines of the same width oriented parallel or perpendicular to one another. In addition, separate but adjacent conductive metal planes used to carry separate signals in a device can capacitively couple when the separation distance between the planes becomes very small resulting in signal degradation and interference between the planes. A method that allows removal of more conductive material between isolated traces therefore can be advantageous in minimizing such interference.

The following definitions are used throughout the specification and claims:

As used herein, the phrase "electrically conductive material" refers to a layer made of a material that is a conductor of electricity, non-limiting examples of which include a pure metal or alloys.

As used herein, the phrase "electrically insulative material" refers to a material that is a nonconductor of electricity.

As used herein, the term "electrode" means a conductor that collects or emits electric charge and controls the movement of electrons. An electrode may include one or more elements attached to a common electrical trace and/or contact pad.

As used herein, the term "electrical component" means a constituent part of the biosensor that has electrical functionality.

As used herein, the phrase "electrode system" refers to an electrical component including at least one electrode, electrical traces and contacts that connect the element with a measuring instrument.

As used herein, the term "electrode element" refers to a constituent part of an electrode system. Specific non-limiting examples of electrode elements include electrodes, contact pads and electrode traces.

As used herein, the phrase "electrode set" is a grouping of at least two electrodes that cooperate with one another to measure the biosensor response.

As used herein, the term "pattern" means a design of one or more intentionally formed gaps, a non-limiting example of which is a single linear gap having a constant width. Not included in the term "pattern" are natural, unintentional defects.

As used herein, the phrase "insulative pattern" means a design of one or more intentionally formed gaps positioned within or between electrically insulative material(s). It is appreciated that electrically conductive material may form the one or more gaps.

As used herein, the phrase "conductive pattern" means a design of one or more intentionally formed gaps positioned within or between electrically conductive material(s). It is appreciated that exposed electrically insulative material may form the one or more gaps.

As used herein, the phrase "microelectrode array" means a group of microelectrodes having a predominantly spherical diffusional characteristic.

As used herein, the phrase "macroelectrode array" means a group of macroelectrodes having a predominantly radial diffusional characteristic.

As used herein, the phrase "electrode pattern" means the relative configuration of the intentionally formed gaps situated between the elements of electrodes in an electrode set specifically or biosensor generally. Non-limiting examples of "electrode patterns" include any configuration of microelectrode arrays, macroelectrode arrays or combinations thereof that are used to measure biosensor response. "Electrode pattern" may also refer to the shape and configuration of all electrical components that are formed on the biosensor.

As used herein, the phrase "feature size" is the smallest dimension of gaps or spaces found in a pattern. For example, in an insulative pattern, the feature size is the smallest dimension of electrically conductive gaps found within or between the electrically insulative material(s). When, however, the pattern is a conductive pattern, the feature size is the smallest dimension of electrically insulative gaps found within or between the electrically conductive material(s). Therefore, in a conductive pattern the feature size represents the shortest distance between the corresponding edges of adjacent elements.

As used herein, the term "interlaced" means an electrode pattern wherein the elements of the electrodes are interwoven relative to one another. In a particular embodiment, interlaced electrode patterns include electrodes having elements, which are interdigitated with one another. In the simplest form, interlaced elements include a first electrode having a pair of elements and a second electrode having a single element received within the pair of elements of the first electrode.

As used herein, the term "ablating" means the removing of material. The term "ablating" is not intended to encompass and is distinguished from loosening, weakening or partially removing the material.

As used herein, the phrase "broad field laser ablation" means the removal of material from a substrate using a laser having a laser beam with a dimension that is greater than the feature size of the formed pattern. Broad field ablation includes the use of a mask, pattern or other device intermediate a laser source and a substrate. The laser is projected through the mask, the latter of which forms an image of an electrode pattern which is projected onto and impinges on the substrate to create all or part of the electrode patterns on the substrate. Broad field laser ablation simultaneously creates the pattern over a significant area of the substrate. The use of broad field laser ablation avoids the need for rastering or other similar techniques that scribe or otherwise define the pattern by continuous movement of a relatively focused laser beam relative to the substrate. A non-limiting example of a process for broad field laser ablation is described below with reference to biosensor 210.

As used herein, the term "line" means a geometric figure formed by a point moving in a first direction along a predetermined linear or curved path and in a reverse direction along the same path. In the present context, an electrode pattern includes various elements having edges that are defined by lines forming the perimeters of the conductive material. Such lines demarcating the edges have desired shapes, and it is a feature of the present invention that the smoothness of these edges is very high compared to the desired shape.

"Theoretical line" as used herein refers to the desired or ideal shape and location of an edge of an electrode element that would be obtained if the manufacturing process were perfect. In most cases, if the edge is straight, the theoretical line will coincide with the average location of the edge.

As used herein, the term "point" means a dimensionless geometric object having no properties except location.

The smoothness or quality of the edge of an electrode element can be defined by the distance that the placement of the edge differs from the theoretical line that represents the perfect or ideal edge. That is, the edge will be spaced from the theoretical line by a distance that varies along the length of the edge. This distance will range from zero to a maximum value. One useful way to define the quality or smoothness of an edge is to simply specify the maximum distance that the edge is spaced from the theoretical line over a specified length of the edge.

The smoothness or quality of an edge can also be specified in terms of the "standard deviation" of the distance between the edge and the theoretical line over a specified length of the edge. To calculate the standard deviation, the distance must be measured at discrete intervals along the length, as described in further detail herein. If the varying distance is denoted "d" and the number of data points is denoted n, then the standard deviation of the distance is calculated as $\{\Sigma(d_i)^2/(n-1)\}^{1/2}$. So that the equation just noted accurately approximates the integral equation from which it is derived, the intervals at which data points are taken should be spaced closely together. All standard deviations expressed herein are measured by taking data points that are spaced by no more than about 20 µm, preferably closer.

As used herein, the term "smoothness standard deviation," when referring to an edge of an electrode element, refers to the standard deviation of the distance that the edge is spaced from a theoretical line over a specified length of the edge. The quality of a gap between electrode elements can be expressed in terms of the individual deviations or standard deviations of the two edges forming the gap from the theoretical lines corresponding to the two edges.

As used herein, the phrase "biological fluid" includes any bodily fluid in which the analyte can be measured, for example, interstitial fluid, dermal fluid, sweat, tears, urine, amniotic fluid, spinal fluid and blood.

As used herein, the term "blood" includes whole blood and its cell-free components, namely plasma and serum.

As used herein, the term "working electrode" is an electrode at which analyte, or product, is electrooxidized or electroreduced with or without the agency of a redox mediator.

As used herein, the term "counter electrode" refers to an electrode that is paired with the working electrode and through which passes an electrochemical current equal in magnitude and opposite in sign to the current passed through the working electrode. The term "counter electrode" is meant to include counter electrodes, which also function as reference electrodes (i.e., a counter/reference or auxiliary electrode).

As used herein, the term "electrochemical biosensor" means a device configured to detect the presence and/or measure the concentration of an analyte by way of electrochemical oxidation and reduction reactions within the biosensor. These reactions are transduced to an electrical signal that can be correlated to an amount or concentration of the analyte.

Additional features of the invention will become apparent to those skilled in the art upon consideration of the following detailed description of the preferred embodiment exemplifying the best mode known for carrying out the invention. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
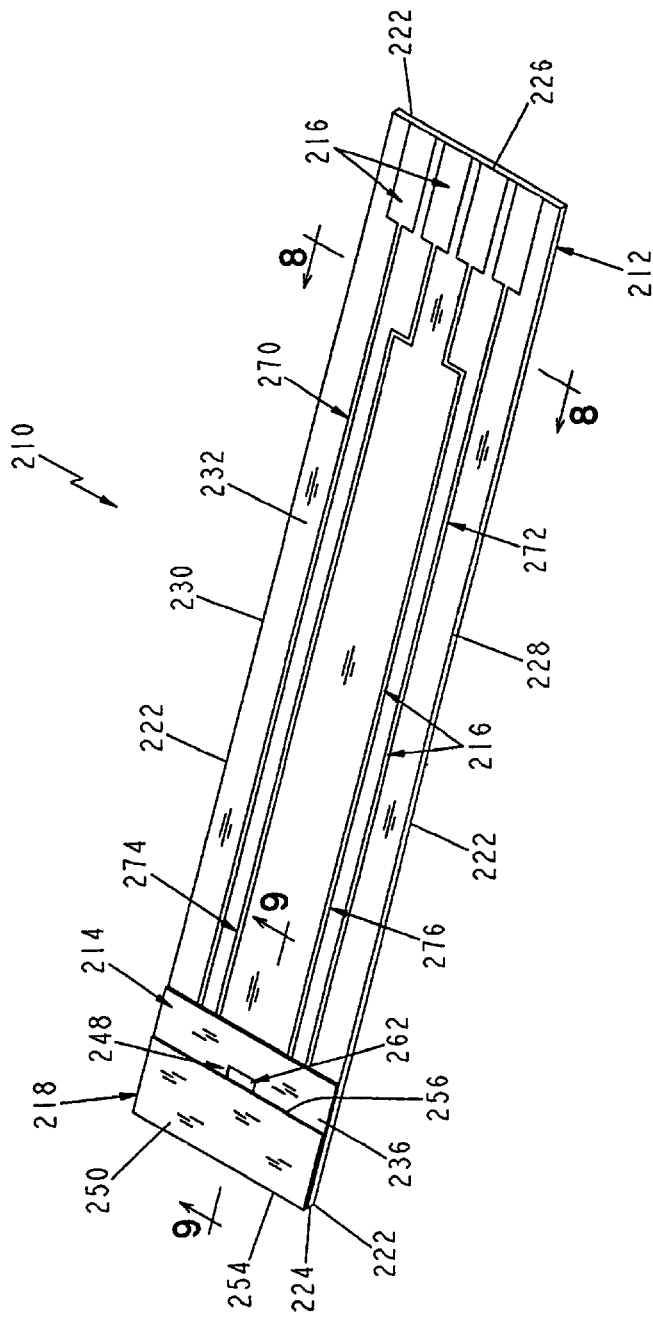
FIG. 1 is a perspective view of a biosensor of the present invention.

For the purposes of promoting an understanding of the principles of the invention, reference will now be made to the embodiments illustrated in the drawings, and specific language will be used to describe the embodiments. It will nevertheless be understood that no limitation of the scope of the invention is intended. Alterations and modifications in the illustrated devices, and further applications of the principles of the invention as illustrated therein, as would normally occur to one skilled in the art to which the invention relates are contemplated, are desired to be protected.

A biosensor in accordance with the present invention provides a surface with electrode patterns formed thereon, the electrode patterns preferably having a smooth edge quality. It is a particular aspect of the present invention that precise quality is obtained for the edges of the electrical components located on the biosensor. Having a smooth or high edge quality of the elements can contribute to greater precision, accuracy, and reproducibility of test results. Further, a smooth or high edge quality also allows for a great number of electrode arrays to be formed on a defined surface area of the biosensor. By increasing the edge quality of the elements, it is possible to increase the number of electrode elements and thus increase the achievable functionality in the defined surface area. These functions may include, for example: multiple measurement electrode pairs for simultaneous measurement of the same or different analytes, including by alternative means; electrodes used to provide correction factors for the basic measurement electrodes; electrodes for detecting dose application or sample sufficiency; multiple electrode traces to monitor electrode functioning or to provide detection or correction of defective traces; and multiple contact pads for coupling to the foregoing functionalities, or for providing additional features such as identification, calibration, or other information pertaining to the biosensor. Further, the selected functionalities for a given biosensor can be provided in a smaller space when the high edge quality allows closer placement of the electrical components. It is a feature of the present invention to enable all of this, and more, in a manner that is relatively fast, reliable and cost effective.

Specifically, a biosensor of the present invention has electrical components with edges that are smooth and are precisely located. The precise locating of the smooth edge is important, particularly relative to a corresponding edge of another electrical component, and especially with respect to a paired element. The importance and the degree of quality of a component's edge quality and placement will vary with the nature of the component.

For macroelectrodes, the edge smoothness and placement are important for the quality of the electrochemical results obtained by use of the macroelectrodes. One factor in the accuracy of such a test is the reproducibility of the area of each macroelectrode. Obtaining precise edge smoothness and placement will yield an area which is highly accurate. Another factor in the use of macroelectrodes is the placement of one of the electrodes relative to the other, e.g., the position of the counter element(s) in relationship to the position of the working element(s). Moreover, since biosensors are generally operated based on calibration methods that rely on the reproducibility of the sizes and locations of the measuring electrodes, the ability to consistently produce lots of such tests trips can enhance the results achieved with the tests.

Similarly, the edge smoothness and placement contribute to the results obtained from microelectrodes. For microelectrodes, the issues can be magnified because of the number and relatively close placement of the numerous microelements. Poor edge quality can greatly affect the operating characteristics of microelectrodes, and the present invention helps to overcome this potential problem. Moreover, an advantage of placing microelements in close proximity is the rapid establishment of steady-state operation. High edge quality and precise edge placement enables closer placement of the elements and in turn faster achievement of steady-state operation. In addition, such closer placement allows for a greater number of microelements to be placed in a given space.

In a first aspect, the present invention provides a high quality edge for the various electrical components on a biosensor. The quality of the edge relates to the smoothness or uniformity of the edge relative to a theoretical profile of the edge. Non-limiting examples of such "smooth" edges formed in accordance with the present invention are shown in FIGS. 21-24.

In one respect, the smoothness relates simply to the deviation of the edge surface relative to the theoretical line defining the desired shape of the edge. It will be appreciated that any electrical component on a biosensor has an intended location and shape that will not be exactly duplicated by the physical embodiment. The extent to which the actual edge of the component varies from the theoretical one is a measure of the smoothness of the edge. As discussed above, this smoothness or quality of the edge can be expressed in terms of the varying distance that the edge is spaced from a theoretical line over a specified length. This distance can be measured at closely spaced intervals, as discussed in detail below, and the standard deviation of the distance can be calculated. Further, the maximum value the distance achieves over a specified length is also a meaningful parameter. For example, in a design where electrodes are to form a gap having a desired width of, e.g., 10 µm, the manufacturing process must be capable of producing edges that will vary by less (preferably much less) than 5 µm over the length of the gap. Otherwise, the electrodes may touch and thus short circuit.

As relates to the various electrical components, the extent to which a given portion of the component is "smooth" may vary. Referring in particular to the measuring electrodes, it will be appreciated that certain edges of the elements are more critical than others. For example, certain edges of the counter and working electrodes are adjacent one another and spaced closely together, while others are not. Also, certain edges are located within the sample-receiving chamber, and others are not. In a first aspect, the present invention relates to providing smooth edges for all of the edges of the measuring electrodes. In another aspect, the invention provides smooth edges particularly for the edges of the measuring electrodes located within the sample-receiving chamber, and more particularly for the edges of the measuring elements that are adjacent to one another. "Adjacent edges" in this context refers to the fact that an edge of a counter element is closest to, i.e., adjacent to, an edge of an element of a working electrode with which the counter electrode is paired.

As indicated previously, the present invention relates in one aspect to providing macroelectrodes having a closely determined area. The desired accuracy of the provided area can vary based on the absolute size of the macroelectrode, as determined by the quality of the edges defining the electrode. Thus, as the smoothness of the edges improves, the difference between the area actually occupied by the electrode and the desired area decreases.

The spacing of macroelectrodes also can benefit from the present invention. For example, for macroelectrodes that are spaced apart by 250 µm, the edges forming the gap preferably have a smoothness standard deviation of less than about 4 µm over the entire length of the edges; for elements spaced apart by 100 µm, the standard deviation is preferably less than about 2 µm.

For microelectrodes, the desired smoothness can differ. For example, for microelements that are spaced apart by 50 µm, the adjacent edges have a smoothness standard deviation of less than about 6 µm, preferably less than about 2 µm, and most preferably less than about 1 µm. If the microelements are spaced apart by about 10 µm, then the smoothness standard deviation is preferably less than about 1 µm, more preferably less than about 0.5 µm. In general, the smoothness standard deviation for microelectrodes is preferably less than about 5% of the width of the gap between adjacent microelements (i.e., feature size), more preferably less than about 2% of the feature size.

It is also an aspect of the present invention that the other electrical components can be provided with smooth edges to facilitate close placement of such components. Such other components preferably have a smoothness standard deviation that is less than about 6 µm, and more preferably less than about 2 µm.

The present invention also provides for the accurate placement of the electrical components relative to one another and to the overall biosensor. The relative placement of components is achieved, at least in part, by the use of broad field laser ablation that is performed through a mask or other device that has a precise pattern for the electrical components. The relative placement of the components therefore does not depend on the controlled movement of a rastering laser or of the substrate relative to the rastering laser. Moreover, this accurate positioning of adjacent edges is further enhanced by the close tolerances for the smoothness of the edges.

Therefore, in a further aspect the invention provides electrical components that have gaps or features that are precisely controlled. More specifically, the electrical components will have designed, theoretical configurations for the gaps between adjacent edges, whereas the physical embodiments will have variations and irregularities. The present invention provides gaps between adjacent edges that are highly uniform. Specifically, the present invention provides a "uniform gap," which is defined as a gap for which the smoothness standard deviation for each edge defining the gap is less than about 6 µm. Preferably, the smoothness standard deviation of both edges defining the gap is less than about 2 µm, more preferably less than about 1 µm.

It is appreciated that the biosensor of the present invention is suitable for use in a system for assessing an analyte in a sample fluid. In addition to the biosensor, the system includes a meter (not shown) and provides methods for evaluating the sample fluid for the target analyte. The evaluation may range from detecting the presence of the analyte to determining the concentration of the analyte. The analyte and the sample fluid may be any for which the test system is appropriate. For purposes of explanation only, a preferred embodiment is described in which the analyte is glucose and the sample fluid is blood or interstitial fluid. However, the present invention clearly is not so limited in scope.

Non-limiting examples of meters suitable for use with the biosensor of the present invention for determination of the analyte in the sample fluid are disclosed in U.S. Pat. Nos. 4,963,814; 4,999,632; 4,999,582; 5,243,516; 5,352,351; 5,366,609; 5,405,511; and 5,438,271, the disclosures of each being incorporated herein by reference. The suitable meter (not shown) will include a connection with electrodes of the biosensor, and circuitry to evaluate an electrochemical signal corresponding to the concentration of the analyte. The meter may also include electrical components that determine whether the sample fluid has been received by the biosensor and whether the amount of sample fluid is sufficient for testing. The meter typically will store and display the results of the analysis, or may alternatively provide the data to a separate device.

The biosensor of the present invention forming part of the system can provide either a qualitative or quantitative indication for the analyte. In one embodiment, the biosensor cooperates with the meter to indicate simply the presence of the analyte in the sample fluid. The biosensor and meter may also provide a reading of the quantity or concentration of the analyte in the sample fluid. In a preferred embodiment, it is a feature of the present invention that a highly accurate and precise reading of the analyte concentration is obtained.

The biosensor is useful for the determination of a wide variety of analytes. The biosensor, for example, is readily adapted for use with any suitable chemistry that can be used to assess the presence of the analyte. Most preferably, the biosensor is configured and used for the testing of an analyte in a biological fluid. Commensurate modifications to the system will be apparent to those skilled in the art. For purposes of explanation, and in a particularly preferred embodiment, the system is described with respect to the detection of glucose in a biological fluid.

The biosensor is also useful with a wide variety of sample fluids, and is preferably used for the detection of analytes in a biological fluid. In addition, the biosensor is useful in connection with reference fluids that are used in conventional fashion to verify the integrity of the system for testing.

In a preferred embodiment, the biosensor is employed for the testing of glucose. The sample fluid in this instance may specifically include, for example, fresh capillary blood obtained from the finger tip or approved alternate sites (e.g., forearm, palm, upper arm, calf and thigh), fresh venous blood, and control solutions supplied with or for the system. The fluid may be acquired and delivered to the biosensor in any fashion. For example, a blood sample may be obtained in conventional fashion by incising the skin, such as with a lancet, and then contacting the biosensor with fluid that appears at the skin surface. It is an aspect of the present invention that the biosensor is useful with very small fluid samples. It is therefore a desirable feature that only a slight incising of the skin is necessary to produce the volume of fluid required for the test, and the pain and other concerns with such method can be minimized or eliminated.

Figure 2:
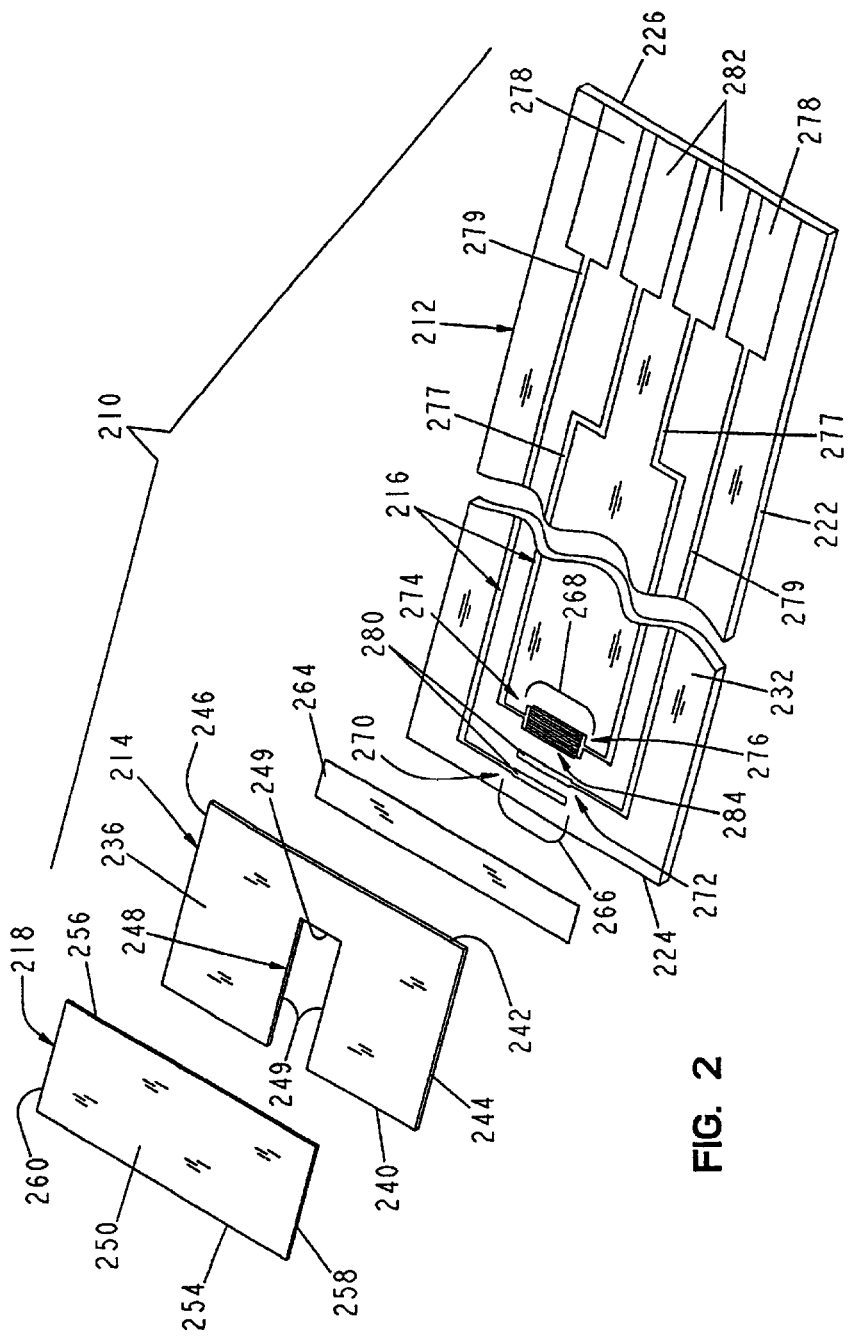
FIG. 2 is an exploded assembly view of the biosensor of FIG. 1.
Figure 9:
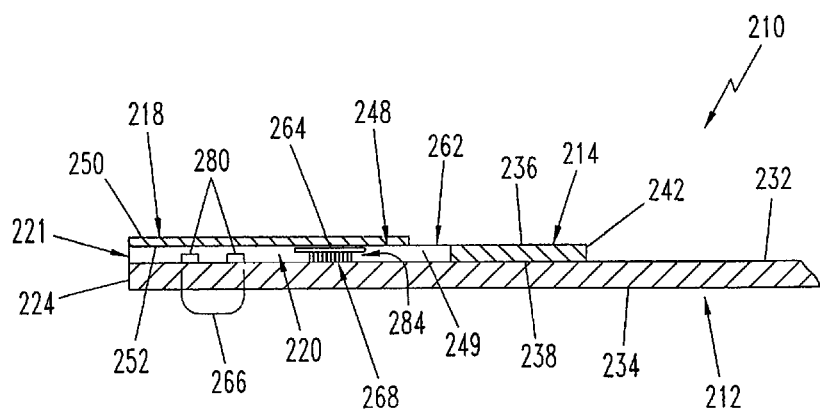
FIG. 9 illustrates a cross-section taken along lines 9-9 of FIG. 1.

Biosensor 210 in accordance with an embodiment of the present invention has two electrode patterns having different feature sizes on a common planar surface and thus permits the accurate measurement of an analyte in a fluid. As shown in FIG. 1, biosensor 210 comprises a base or base substrate 212, conductive material 216 positioned on the base 212, a spacer 214, and a cover 218. The cover 218 and spacer 214 cooperate with the base 212 to define a sample-receiving chamber 220 (FIG. 9) having a sample inlet opening 221 for the sample fluid, and a reagent 264 for producing an electrochemical signal in the presence of a test analyte. The biosensor 210 is formed as a test strip, particularly one having a laminar construction providing an edge or surface opening to the sample-receiving chamber 220. The reagent 264, as shown in FIGS. 2 and 9, is exposed by the sample-receiving chamber 220 to provide the electrochemical signal to a working electrode also positioned within the chamber 220. In appropriate circumstances, such as for glucose detection, the reagent may contain an enzyme and optionally a mediator.

Figure 8:
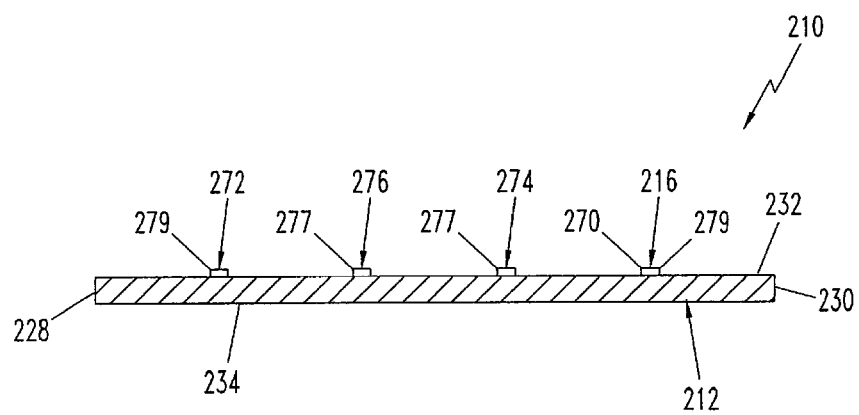
FIG. 8 illustrates a cross-section taken along lines 8-8 of FIG. 1.

The base 212 of biosensor 210 includes edges 222 that define opposite ends 224, 226 and sides 228, 230 extending between the ends 224, 226. Base 212 also has a top surface 232 supporting the conductive material 216 and an opposite bottom surface 234 (FIGS. 8 and 9). Illustratively, base 212 has a length of 40 mm and a width of 10 mm. It is appreciated, however that these values are merely illustrative and that the dimensions of the base 212 may vary in accordance with the present disclosure.

The base 212 is a substrate that is formed from an insulating material, so that it will not provide an electrical connection between electrodes formed from the conductive material 216. Non-limiting examples of suitable insulating materials include glass, ceramics and polymers. Preferably, the base is a flexible polymer and has a strong absorbance in the UV. Non-limiting examples of suitable materials include polyethylene terephthalate (PET), polyethylene naphthalate (PEN), and polyimide films. The suitable films are commercially available as MELINEX®, KALADEX® and KAPTON®, respectively from E.I. duPont de Nemours, Wilmington, Del., USA ("duPont") and UPILEX®, a polyimide film from UBE Industries Ltd, Japan. Preferred materials are selected from 10 mil thick MELINEX® 329 or KAPTON®, which are coated with 50±4 nm gold within-lot C.V. of <5% by: Techni-Met Advanced Depositions, Inc., Windsor, Conn., USA. It is appreciated that the base 212 may be either purchased pre-coated with conductive material 216 or may be coated by sputtering or vapor deposition, in accordance with this disclosure. It is further appreciated that the thickness of the conductive material can vary in accordance with this disclosure.

Spacer 214 is illustratively positioned on the top surface 232 of the base 212 adjacent to end 224. Spacer 214 has an upper surface 236 and a lower surface 238 (FIG. 9) facing the base 212. Referring now to FIG. 2, the spacer 214 has edges 240, 242, 244, 246. Illustratively, spacer 214 has a length of about 6 mm, a width of about 10 mm and a height of about 4 mil. It is appreciated, however that these values are merely illustrative and that the biosensor may be formed without a spacer and that the dimensions of the spacer 214 may vary in accordance with the present disclosure.

Spacer 214 is formed from an insulating material, so that it will not provide an electrical connection between electrodes formed from the conductive material 216. Non-limiting examples of suitable insulating materials include glass, ceramics, polymers, photoimageable coverlay materials, and photoresists—non-limiting examples of which are disclosed in U.S. patent application Serial No. Ser. No. 10/264,891, filed Oct. 4, 2002, the disclosure of which is incorporated herein by reference. Illustratively, spacer 214 is formed of 4 mil MELINEX® polyester film, which is preferred for use with whole blood samples. It is appreciated, however, that when the sample is plasma or serum, 1-2 mil film may be preferred for use in accordance with this disclosure. It is appreciated, however that these values are merely illustrative and that the composition and dimension of the spacer 214 may vary in accordance with the desired height of the sample-receiving chamber.

A slit or void 248 is formed in the spacer 214 and extends from the edge 240 toward the edge 242. The slit 248 defines at least the length and width of the sample-receiving chamber 220 and is defined by edges 249. Illustratively, the slit 248 has a length of 5 mm, a width of 1 mm, and a height of 0.1 mm, but may have a variety of lengths and widths in accordance with the present disclosure. It is further appreciated that the edges 249 of the slit may also be curved or angular in accordance with this disclosure.

As shown in FIG. 1, the cover 218 is positioned on the upper surface 236 of spacer 214. Cover 218 has a first surface 250 and a second surface 252 (FIG. 9) facing the base 212. Further, the cover 218 has edges 254, 256, 258, 260. As shown in FIG. 1, the cover 218 has a length that is less than the length of the slit 248. Illustratively, cover 218 has a length of about 4 mm, a width of about 10 mm and a height of about 0.1 mm. It is appreciated, however that these values are merely illustrative and that the biosensor may be formed without a cover and that the dimensions of the cover 218 may vary in accordance with the present disclosure.

The cover 218 is illustratively formed of a clear material having a hydrophilic adhesive layer in proximity to the spacer. Non-limiting examples of materials suitable for cover 218 include polyethylene, polypropylene, polyvinylchloride, polyimide, glass, or polyester. A preferred material for cover 218 is 100 µm polyester. A preferred adhesive is ARCare 8586 having a MA-55 hydrophilic coating, commercially available from Adhesives Research Inc., Glen Rock, Pa. Further, it is appreciated that the cover may have markings in accordance with this disclosure.

The slit 248 in the spacer 214, together with the cover 218, and the base 212, form the sample-receiving chamber 220 (FIG. 9), which acts to expose reagent 264 to a fluid to be tested from a user of biosensor 210. This sample-receiving chamber 220 can act as a capillary channel, drawing the fluid to be tested from the opening 221 onto a sensing region of the conductive material 216 and toward a vent 262. It is appreciated that the biosensor may be formed without a spacer in accordance with this disclosure and that in addition to or instead of the spacer and the cover, a variety of dielectric materials may cover the base 212 exposing only selected portions of the conductive material in accordance with this disclosure. Moreover, it is appreciated that when present, the dimensions of the channel 220 may vary in accordance with this disclosure.

FIG. 2 illustrates the conductive material 216 defining electrode systems comprising a first electrode set 266 and a second electrode set 268, and corresponding traces 279, 277 and contact pads 278, 282, respectively. The conductive material 216 may contain pure metals or alloys, or other materials, which are metallic conductors. Preferably, the conductive material is transparent at the wavelength of the laser used to form the electrodes and of a thickness amenable to rapid and precise processing. Non-limiting examples include aluminum, carbon, copper, chromium, gold, indium tin oxide (ITO), palladium, platinum, silver, tin oxide/gold, titanium, mixtures thereof, and alloys or metallic compounds of these elements. Preferably, the conductive material includes noble metals or alloys or their oxides. Most preferably, the conductive material includes gold, palladium, aluminum, titanium, platinum, ITO and chromium. The conductive material ranges in thickness from about 10 nm to 80 nm, more preferably, 30 nm to 70 nm. FIGS. 1-3, 6, and 8-9 illustrate the biosensor 210 with a 50 nm gold film. It is appreciated that the thickness of the conductive material depends upon the transmissive property of the material and other factors relating to use of the biosensor.

Illustratively, the conductive material 216 is ablated into two electrode systems that comprise sets 266, 268. In forming these systems, the conductive material 216 is removed from at least about 5% of the surface area of the base 212, more preferably at least about 50% of the surface area of the base 212, and most preferably at least about 90% of the surface area of the base 212. As shown in FIG. 2, the only conductive material 216 remaining on the base 212 forms at least a portion of an electrode system.

While not illustrated, it is appreciated that the resulting patterned conductive material can be coated or plated with additional metal layers. For example, the conductive material may be copper, which is then ablated with a laser, into an electrode pattern; subsequently, the copper may be plated with a titanium/tungsten layer, and then a gold layer, to form the desired electrodes. Preferably, a single layer of conductive material is used, which lies on the base 212. Although not generally necessary, it is possible to enhance adhesion of the conductive material to the base, as is well known in the art, by using seed or ancillary layers such as chromium nickel or titanium. In preferred embodiments, biosensor 210 has a single layer of gold, palladium, platinum or ITO.

As shown in FIGS. 2 and 9, the biosensor 210 includes an electrode system comprising at least a working electrode and a counter electrode within the sample-receiving chamber 220. The sample-receiving chamber 220 is configured such that sample fluid entering the chamber is placed in electrolytic contact with both the working electrode and the counter electrode. This allows electrical current to flow between the electrodes to effect the electrooxidation or electroreduction of the analyte or its products.

Figure 3:
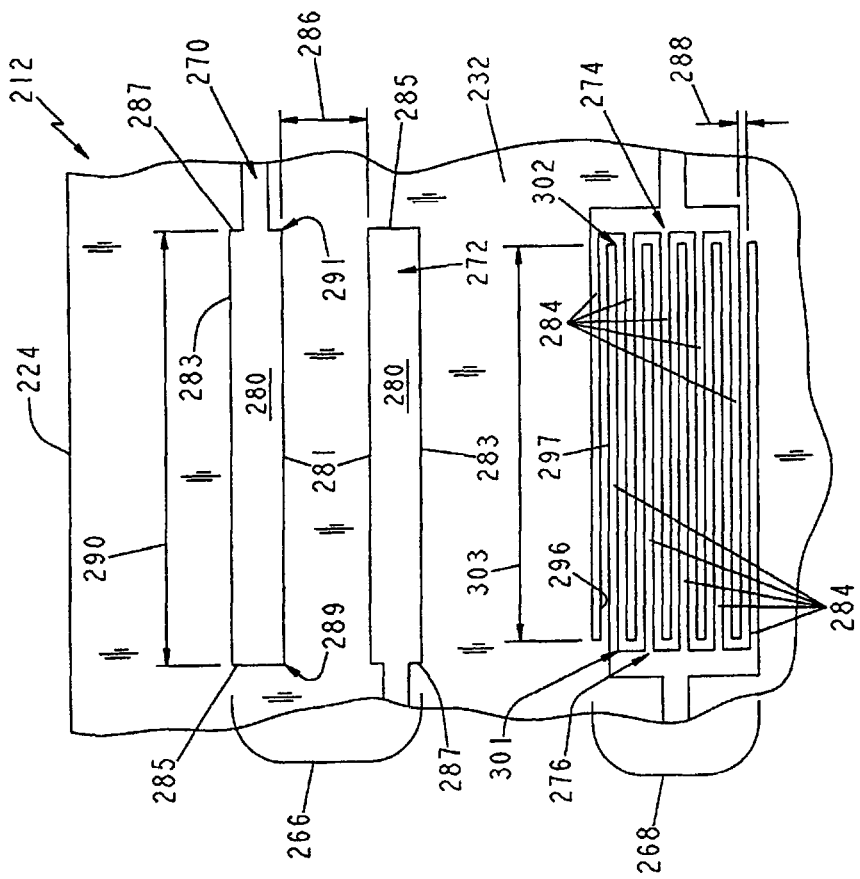
FIG. 3 is an enlarged plan view of the biosensor of FIG. 1 showing a macroelectrode array and a microelectrode array.

Referring now to FIG. 3, the first electrode set 266 of the electrode system includes two electrodes 270, 272. Illustratively, electrode 270 is a working electrode and electrode 272 is a counter electrode. The electrodes 270, 272 each have a single element or finger 280 that is in communication with a contact pad 278 via a connecting trace 279 (shown in FIG. 2). The electrode fingers 280 of the electrodes 270, 272 cooperate to define an electrode pattern formed as a macroelectrode array. It is appreciated, as will be discussed hereafter, that the electrodes 270, 272 can include more than one finger each in accordance with this disclosure. It is further appreciated that the shape, size and relative configuration of the electrodes or electrode fingers may vary in accordance with the present disclosure.

As shown in FIG. 2, the second electrode set 268 includes two electrodes 274, 276. Illustratively, electrode 274 is a working electrode and electrode 276 is a counter electrode. Further, the electrodes 274, 276 each have five electrode elements or fingers 284 that are in communication with a contact pad 282 via a connecting trace 277. Referring now to FIG. 3, the electrode fingers 284 cooperate to define an electrode pattern formed as an interlaced microelectrode array. While five electrode fingers 284 are illustrated, it is appreciated that the elements of electrodes 274, 276 can each be formed with greater or fewer than five electrode fingers in accordance with this disclosure. It is further appreciated that the shape, size and relative configuration of the electrodes may vary in accordance with the present disclosure.

It is appreciated that the values for the dimensions of the electrode sets 266, 268 as illustrated in FIG. 2 are for a single specific embodiment, and these values may be selected as needed for the specific use. For example, the length of the electrode sets may be any length up to the length of the base, depending upon the orientation of the electrode sets on the base. Further, it is appreciated that the width of the conducting traces in communication with the electrode sets may vary, a non-limiting example of which is from about 0.4 mm to about 5 mm. It is further appreciated that the width of each contact pad may vary, a non-limiting example of which is from about 1 mm to about 5 mm. The electrode patterns shown in FIG. 2 are symmetric, however this is not required, and irregular or asymmetric patterns (or electrode shapes) are possible in accordance with this disclosure. Further, the number of electrode sets on the base 212 may vary, and therefore each base 212 can contain, for example 1 to 1000 electrode sets, preferably 2 to 20 electrode sets, more preferably 2 to 3 electrode sets.

Referring again to the first electrode set 266 of FIG. 3, each electrode finger 280 is defined by an inner edge 281, an outer edge 283, and opposite third and fourth edges 285, 287. Each edge 218, 283, 285, 287 has a smooth edge quality. As discussed earlier, the edge quality of the electrodes 270, 272 is defined by the edge's deviation from a theoretical line extending between first and second points. The following description of deviations can apply to each edge of electrodes 270, 272 of biosensor 210. For clarity purposes, however, only the edge 281 of electrode 270 will be discussed hereafter.

As shown in FIG. 3, the edge 281 of electrode 270 extends between points 289, 291 located on the base 212. Points 289, 291 are located at opposite ends of the inner edge 281, which represents the entire length of the gap 286 between electrodes 280. It is appreciated that the points 289, 291 may be positioned at a variety of locations and at a variety of distances relative to one another depending upon the length of the desired edge in accordance with this disclosure. However, the length of interest will typically be the entire length over which a gap extends, since the smoothness of the adjacent edges is normally most important over this entire length.

Figure 4:
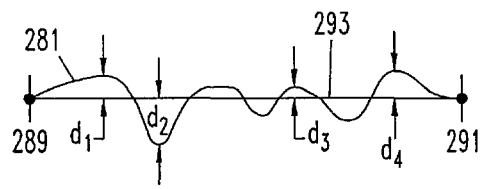
FIG. 4 is a diagram of the deviation of an edge of an electrode element from a theoretical or ideal line representing the desired shape and placement of the edge.

FIG. 4 illustrates the theoretical line 293 that extends exactly between points 289, 291. That is, line 293 represents the ideal or desired edge that would be obtained if the process of forming the electrodes were perfect. However, at any given point along the length of line 293, the edge 281 will be spaced in either direction from theoretical line 293 by a distance "$d_i$." The distance $d_i$ varies from zero to a maximum value depending upon where it happens to be measured, as shown, e.g., with reference to distances $d_1$, $d_2$, $d_3$ and $d_4$ in FIG. 4. A standard deviation of this distance over the length of line 293 is less than about 6 µm in accordance with this disclosure, creating an edge with a smooth edge quality. In preferred embodiments, the standard deviation of the edge 281 from theoretical line 293 is less than 2 µm, and most preferably less than 1.0 µm. An example of this deviation from mean or theoretical is illustrated in FIG. 10.

Figure 10:
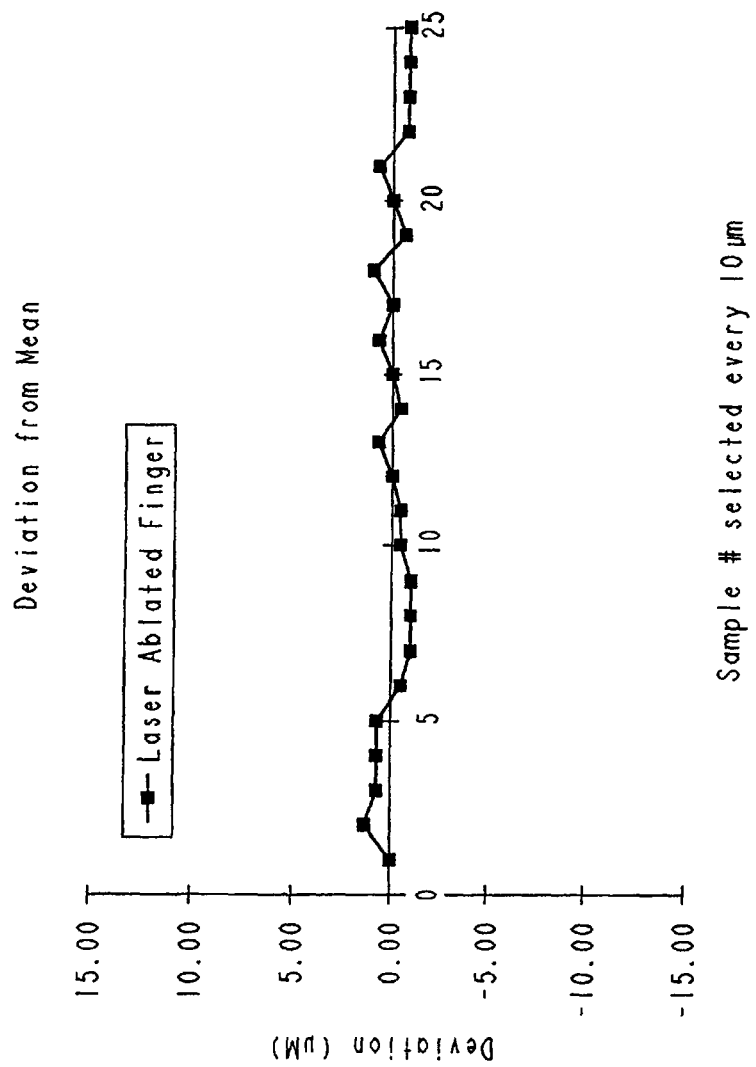
FIG. 10 is a graph showing the deviation from mean or theoretical of an electrode edge of the microelectrode array of FIG. 3.

The edge quality illustrated in FIG. 10 was measured using Micro-Measure system commercially available from LPKF Laser Electronic GmbH, of Garbsen, Germany with Metric 6.21 software. The Metric software allows the display and measuring of video images on a PC. Measurements were made by capturing the image and then allowing the software to place a 10 µm grid over the image. The grid was aligned with the edge by moving the electrode structure under the measurement objective. (By physically manipulating the image, the edge can be vertically aligned to be parallel with the grid.) Using the software, measurements from the grid line to the electrode edge were then made at 10 µm intervals along the length of a line 250 µm long using a point-to-point process. The effective video magnification to video screen was 575×. (Using objective Q750). Video magnification=Actual measured "Scale length" on the video screen (µm)/Scale value (µm). For example, 115000 µm/200 µm=575×.

In one analysis of an electrical pattern formed using the principles of the present invention, the deviation from mean of the edges was measured using a QVH-606 PRO Vision Measuring System (computer-controlled non-contact measurement system), commercially available from Mitutoyo America Corporation, Aurora, Ill. with an effective magnification to video screen=470×. Standard deviations were calculated from measurements made at an average interval of 0.69 µm for a length of at least 250 µm. Other settings: Ring lighting (Intensity 89, Position 60), Edge Detection (Edge Slope=Falling, Edge Detection TH=169, THS=18.5, THR=0.5 Scan Interval=1). The standard deviation from the mean value was less than about 2 µm.

Referring again to FIG. 4, the line 293 is illustratively a straight line. It is appreciated, however, that the shape of the line 293 may be curved or angular, so long as the standard deviation of the distance of edge 281 from that line 293 over the length of the edge is less than about 6 µm.

The electrode fingers 280, as shown in FIG. 3, are separated from one another by an electrode gap 286, which corresponds to the feature size of the electrode pattern of the electrode set 266. The electrode gap 286 shown in FIG. 3 is shown as formed by two straight edges 281. However, as just noted, the placement of edges 281 varies from theoretical value 293 (FIG. 4) by a distance that varies along the length of the edge. Illustratively, in biosensor 210, the electrically insulative material of the top surface 232 is exposed between the electrode fingers 280 along a length 290. It is appreciated, however, that rather than top surface 232 being exposed, the base can be coated with materials, or recesses can be formed between the electrodes as disclosed in U.S. patent application Ser. No. 09/704,145, filed on Nov. 1, 2000, now U.S. Pat. No. 6,540,890, the disclosure of which is incorporated herein by reference.

Figure 5:
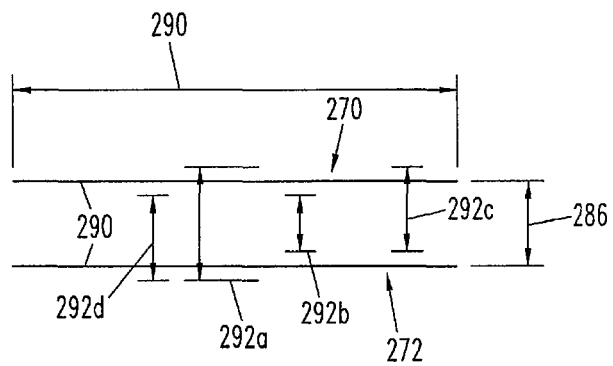
FIG. 5 is a diagram of the deviation in gap width and placement resulting from the deviations in the two individual edges forming the gap.

As shown in FIGS. 3 and 5, the inner edges 281 of electrode fingers 280 have an equal length, illustrated by the numeral 290 and are separated from one another by the electrode gap 286, whose length is also represented by length 290. Because the two edges 281 defining gap 286 are not perfect, gap 286 will in fact vary in width and placement over its length, as shown with reference to gaps 292a-292d in FIG. 5. When the deviations of the two edges defining gap 286 are in the same direction, they tend to cancel each other as to width deviation, at least in part, and cause a net shift in placement of the gap, as illustrated with respect to reference numerals 292c and 292d of FIG. 5. A theoretical gap can be defined by two theoretical lines 293 associated with edges 281. The quality of the gap or its deviation from the theoretical gap can be specified in terms of the quality of the two individual edges defining it. Preferably, the smoothness standard deviation of both edges defining gap 286 is less 6 µm, preferably less than 2.0 µm, and most preferably less than 1 µm.

Figure 6:
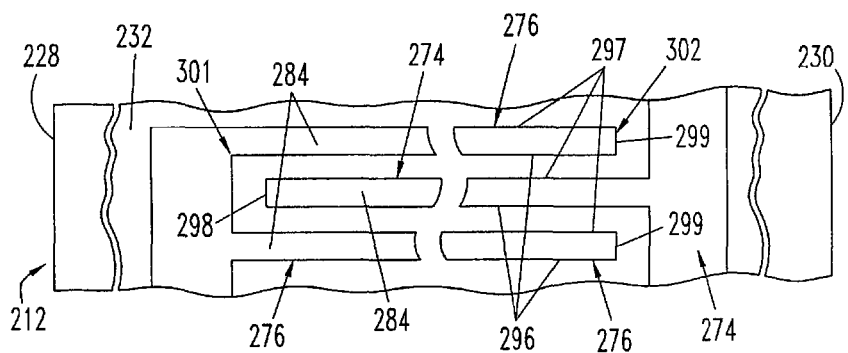
FIG. 6 is an enlarged section of the microelectrode array of FIG. 3.

The electrode fingers 284, which define the elements of electrodes 274, 276 are illustrated in FIGS. 3 and 6. For clarity purposes, however, only three of these electrode fingers 284 will be discussed hereafter as they are illustrated in FIG. 6. Each electrode finger 284 is defined by a first edge 296 and a second edge 297. Further, adjacent fingers 284 have spaced-apart third and fourth edges 298, 299 respectively. These edges 296, 297, 298, 299 of fingers 284 can also have a smooth edge quality. As previously described with reference to electrodes 270, 272, the edge quality of the electrodes 274, 276 is defined by the respective edge's deviation from a line extending between first and second points. The following description of deviations will apply to each edge of electrode fingers 284 of biosensor 210. For clarity purposes, however, only one edge 296 of electrode finger 284 will be discussed hereafter.

Figure 7:
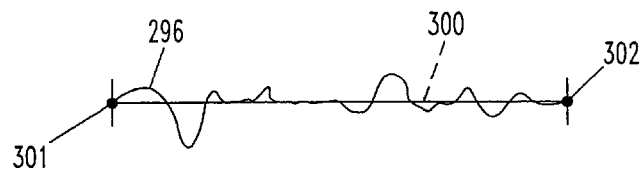
FIG. 7 is a diagram of the deviation of an edge of an electrode element from a theoretical or ideal line representing the desired shape and placement of the edge.

The edge 296 of electrode finger 284 extends between first and second points 301, 302 located on the base 212. As shown in FIG. 7, a theoretical line 300 extends exactly between points 301, 302, which is typically the length of the gap formed by edge 296 and 297. A standard deviation of the varying distance of edge 296 from line 300 is less than about 6 µm, in accordance with this disclosure, creating an edge with a smooth edge quality. In preferred embodiments, the standard deviation of the edge 296 from theoretical line 300 is less than 2 µm, and most preferably less than 1.0 µm. Illustratively, the line 300 is a straight line. It is appreciated, however, that the shape of the line 300 may be curved or angular. It is also appreciated that the specific positions of first and second locations 300, 301 on the surface 232 may vary in accordance with the disclosure, although the lengths of most importance are typically the entire length of the gaps between these closely spaced electrode fingers.

Referring again to FIG. 3, the electrode fingers 284 are separated from one another by an electrode gap 288, which corresponds to the feature size of the electrode pattern of the electrode set 268. The electrode gap 288 relates to the width between adjacent edges 296, 297 of fingers 284. Because the two edges defining gap 288 are not perfect, gap 288 will in fact vary in position and placement over its length. Illustratively, in biosensor 210, the electrically insulative material of the base 212 is exposed between the electrode fingers 284 along a length 303. It is appreciated, however, that rather than top surface 232 being exposed, the base can be coated with materials, or recesses can be formed between the electrodes as disclosed in U.S. patent application Ser. No. 09/704,145, filed on Nov. 1, 2000, now U.S. Pat. No. 6,540,890, entitled "Biosensor", the disclosure of which is incorporated herein by reference.

The electrode gap 288, which corresponds to the feature size of the electrode pattern of the electrode set 268 is different than the feature size of the electrode pattern of the electrode set 266. Illustratively, the feature size, or gap 288 between the electrode fingers 284 has a width of about 100 µm or less, including about 1 µm to about 100 µm, even more preferably 75 µm or less, including about 17 µm to about 50 µm. It is appreciated that the electrode gap for a microelectrode array can vary. For example, it is understood that the electrode gap can be less than 1 µm in accordance with the present disclosure. The size of the achievable gap is dependent upon the quality of the optics, the wavelength of the laser, and the window size of a mask field.

As illustrated in FIG. 3, the gap 288 has a width along a length 303 of the opposing edges 296, 297 of the electrode fingers 284. Like gap 286, the quality of gap 286 or its deviation from a theoretical gap can be specified in terms of the quality of the two individual edges defining it. Preferably, the smoothness standard deviation of both edges defining gap 286 is less 6 µm, preferably less than 2.0 µm, and most preferably less than 1 µm.

Referring now to FIG. 9, the electrode fingers 284 are covered with the reagent 264 and may be used to provide electrochemical probes for specific analytes. The starting reagents are the reactants or components of the reagent, and are often compounded together in liquid form before application to the ribbons or reels, or in capillary channels on sheets of electrodes. The liquid may then evaporate, leaving the reagent in solid form. The choice of a specific reagent depends on the specific analyte or analytes to be measured, and is not critical to the present invention. Various reagent compositions are well known to those of ordinary skill in the art. It is also appreciated that the placement choice for the reagent on the base may vary and depends on the intended use of the biosensor. Further, it is appreciated that the techniques for applying the reagent onto the base may vary. For example, it is within the scope of the present disclosure to have the reagent screen-printed onto the fingers.

A non-limiting example of a dispensable reagent for measurement of glucose in a human blood sample contains 62.2 mg polyethylene oxide (mean molecular weight of 100-900 kilodaltons), 3.3 mg NATROSOL 250 M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase, forming a solution of quinoprotein glucose dehydrogenase. This reagent is further described in U.S. Pat. No. 5,997,817, the disclosure of which is expressly incorporated herein by reference.

A non-limiting example of a dispensable reagent for measurement of hematocrit in a sample contains oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F—a blend of 88% microcrystalline cellulose and 12% sodium carboxymethyl—cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is expressly incorporated herein by reference.

Non-limiting examples of enzymes and mediators that may be used in measuring particular analytes in biosensors of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensors in accordance with this disclosure.

Another non-limiting example of a suitable dispensable reagent for use with biosensors of the present invention is nitrosoanaline reagent, which includes a PQQ-GDH and para-Nitroso-Aniline mediator. A protocol for the preparation of the nitrosoanaline reagent is the same in all respects as disclosed in U.S. patent application Ser. No. 10/688,312, entitled "System And Method For Analyte Measurement Using AC Phase Angle Measurement", filed Oct. 17, 2003, the disclosure of which is incorporated herein by reference. The reagent mass composition—prior to dispensing and drying is as set forth in Table 2.

TABLE 2

| | Component | % w/w | Mass for 1 kg |
|---|---|---|---|
| solid | Polyethylene oxide (300 KDa) | 0.8054% | 8.0539 g |
| solid | NATROSOL ® 250 M | 0.0470% | 0.4698 g |
| solid | AVICEL ® RC-591F | 0.5410% | 5.4104 g |

TABLE 2-continued

| | Component | % w/w | Mass for 1 kg |
|---|---|---|---|
| solid | Monobasic potassium phosphate (anhydrous) | 1.1437% | 11.4371 g |
| solid | Dibasic potassium phosphate (anhydrous) | 1.5437% | 15.4367 g |
| solid | Sodium Succinate hexahydrate | 0.5876% | 5.8761 g |
| solid | Potassium Hydroxide | 0.3358% | 3.3579 g |
| solid | Quinoprotein glucose dehydrogenase (EncC#: 1.1.99.17) | 0.1646% | 1.6464 g |
| solid | PQQ | 0.0042% | 0.0423 g |
| solid | Trehalose | 1.8875% | 18.8746 g |
| solid | Mediator BM 31.1144 | 0.6636% | 6.6363 g |
| solid | TRITON ® X-100 | 0.0327% | 0.3274 g |
| solvent | Water | 92.2389% | 922.3888 g |

% Solids 0.1352687
Target pH 6.8
Specific Enzyme Activity Used (U/mg 689 DCIP
Dispense Volume per Biosensor 4.6 mg A coatable reagent suitable for use with the present disclosure is as follows in Table 3.

TABLE 3

| Component | % w/w | Mass for 1 kg |
|---|---|---|
| Keltrol F, xanthan gum | 0.2136% | 2.1358 g |
| Sodium Carboxymethylcellulose (CMC) | 0.5613% | 5.6129 g |
| Polyvinylpyrrolidone, (PVP K25) | 1.8952% | 18.9524 g |
| PROPIOFAN ®, | 2.8566% | 28.5657 g |
| GlucDOR | 0.3310% | 3.3098 g |
| PQQ | 0.0092% | 0.0922 g |

TABLE 3-continued

| Component | % w/w | Mass for 1 kg |
|---|---|---|
| Sipernat 320 DS | 2.0039% | 20.0394 g |
| Na-Succinat x 6H2O | 0.4803% | 4.8027 g |
| Trehalose | 0.4808% | 4.8081 g |
| $KH_2PO_4$ | 0.4814% | 4.8136 g |
| $K_2HPO_4$ | 1.1166% | 11.1658 g |
| Mediator 31.1144 | 0.6924% | 6.9242 g |
| Mega 8 | 0.2806% | 2.8065 g |
| Geropon T 77 | 0.0298% | 0.2980 g |
| KOH | 0.1428% | 1.4276 g |
| Water | 88.4245% | 884.2453 g |

% Solids 11.5755
Target pH 7.0
Specific Enzyme Activity Used (U/mg 2.23 DCIP
Coat Weight 55 g/m²

Figure 17:
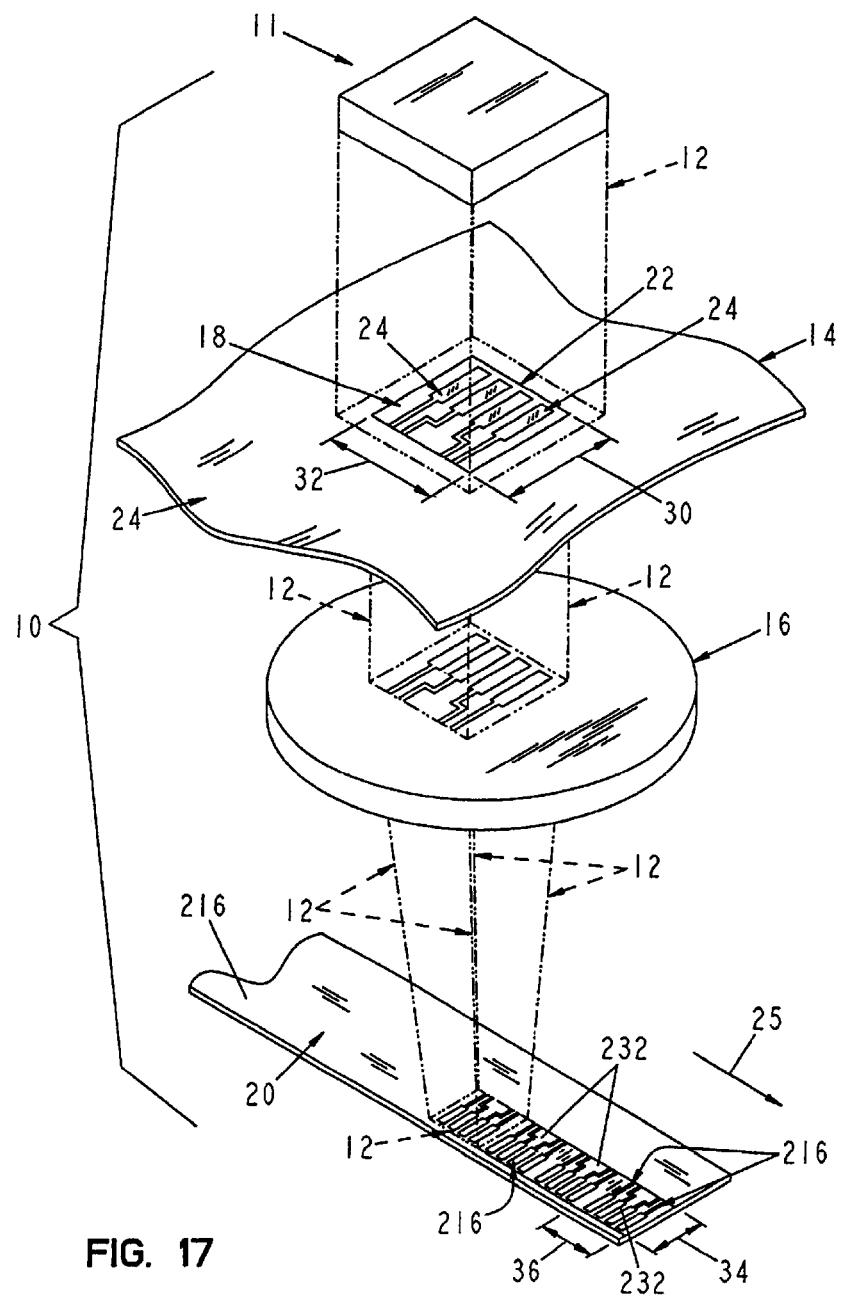
FIG. 17 is a view of an ablation apparatus suitable for use with the present invention.
Figure 18:
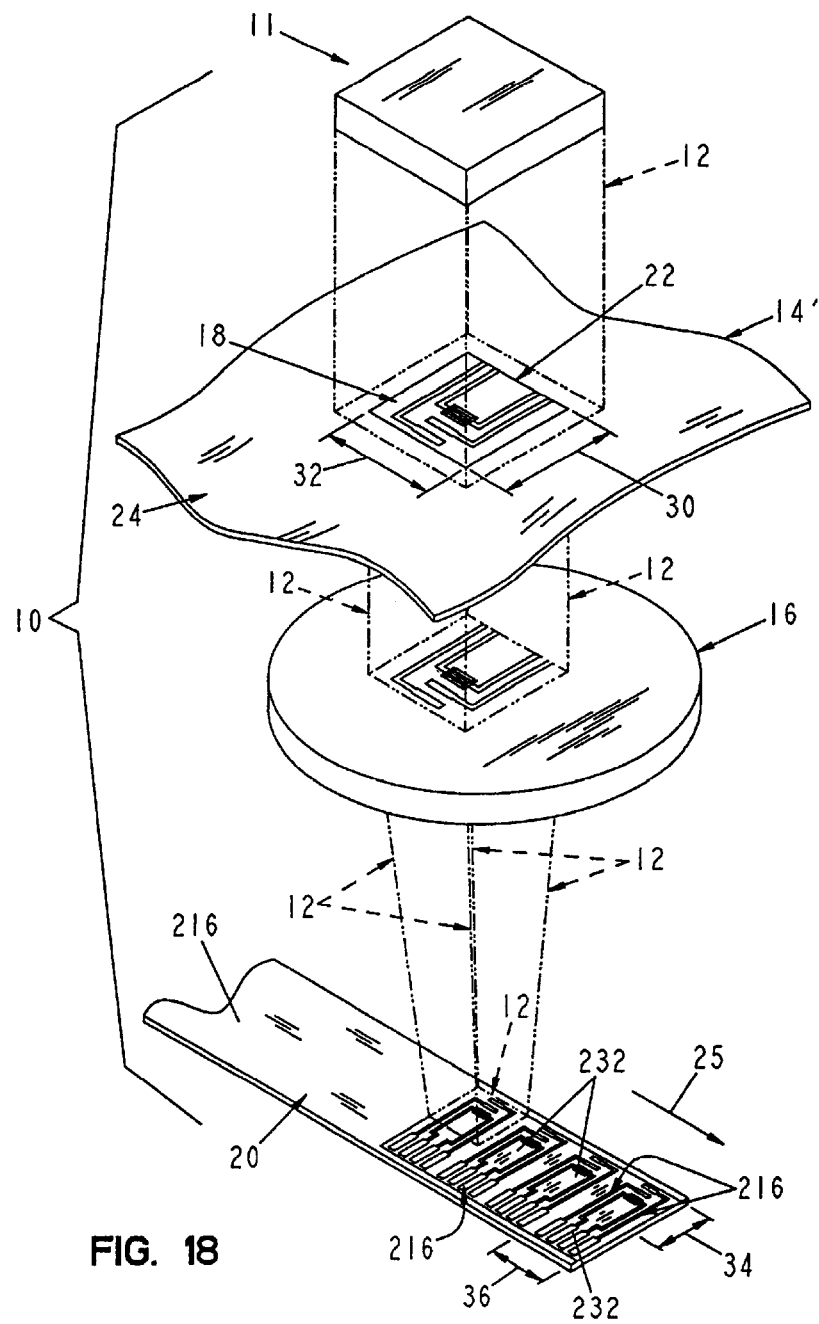
FIG. 18 is a view of the laser ablation apparatus of FIG. 17 showing a second mask.
Figure 19:
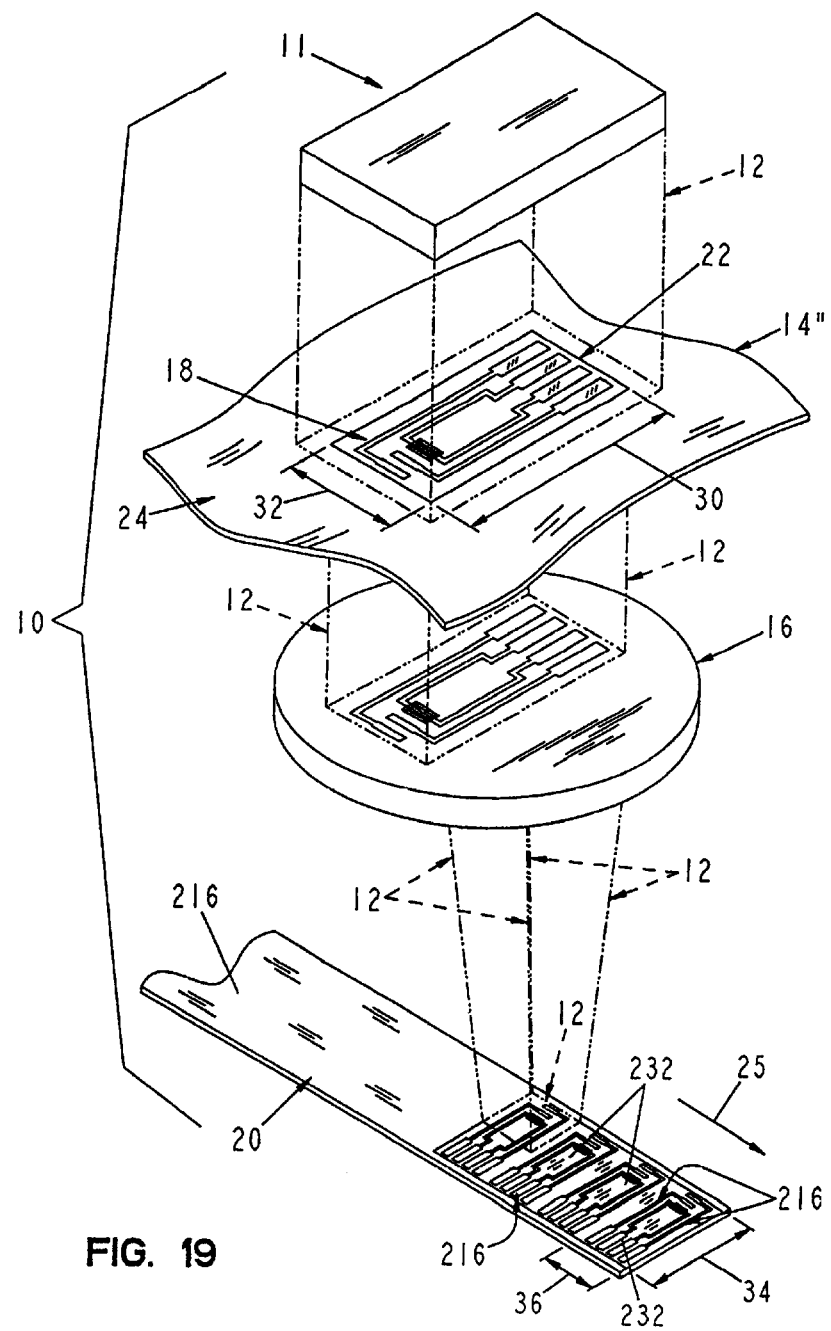
FIG. 19 is a view of an ablation apparatus suitable for use with the present invention.

Biosensor 210 is illustratively manufactured using two apparatuses 10, 10', shown in FIGS. 17-18 and 19, respectively. It is appreciated that unless otherwise described, the apparatuses 10, 10' operate in a similar manner. Referring first to FIG. 17, biosensor 210 is manufactured by feeding a roll of ribbon or web 20 having an 80 nm gold laminate, which is about 40 mm in width, into a custom fit broad field laser ablation apparatus 10. The apparatus 10 comprises a laser source 11 producing a beam of laser light 12, a chromium-plated quartz mask 14, and optics 16. It is appreciated that while the illustrated optics 16 is a single lens, optics 16 is preferably a variety of lenses that cooperate to make the light 12 in a pre-determined shape or image that is then projected onto the web of base substrate 20.

A non-limiting example of a suitable ablation apparatus 10 (FIGS. 17-18) is a customized MicrolineLaser 200-4 laser system commercially available from LPKF Laser Electronic GmbH, of Garbsen, Germany, which incorporates an LPX-400, LPX-300 or LPX-200 laser system commercially available from Lambda Physik AG, Gottingen, Germany and a chromium-plated quartz mask commercially available from International Phototool Company, Colorado Springs, Co.

For the MicrolineLaser 200-4 laser system (FIGS. 17-18), the laser source 11 is a LPX-200 KrF-UV-laser. It is appreciated, however, that higher wavelength UV lasers can be used in accordance with this disclosure. The laser source 11 works at 248 nm, with a pulse energy of 600 mJ, and a pulse repeat frequency of 50 Hz. The intensity of the laser beam 12 can be infinitely adjusted between 3% and 92% by a dielectric beam attenuator (not shown). The beam profile is 27×15 mm² (0.62 sq. inch) and the pulse duration 25 ns. The layout on the mask 14 is homogeneously projected by an optical elements beam expander, homogenizer, and field lens (not shown). The performance of the homogenizer has been determined by measuring the energy profile. The imaging optics 16 transfer the structures of the mask 14 onto the ribbon 20. The imaging ratio is 2:1 to allow a large area to be removed on the one hand, but to keep the energy density below the ablation point of the applied chromium mask on the other hand. While an imaging of 2:1 is illustrated, it is appreciated that the any number of alternative ratios are possible in accordance with this disclosure depending upon the desired design requirements. The ribbon 20 moves as shown by arrow 25 to allow a number of layout segments to be ablated in succession.

The positioning of the mask 14, movement of the ribbon 20, and laser energy are computer controlled. As shown in FIG. 17, the laser beam 12 is projected onto the ribbon 20 to be ablated. Light 12 passing through the clear areas or windows 18 of the mask 14 ablates the metal from the ribbon 20. Chromium coated areas 24 of the mask 14 blocks the laser light 12 and prevent ablation in those areas, resulting in a metallized structure on the ribbon 20 surface. Referring now to FIG. 18, a complete structure of electrical components may require additional ablation steps through a second mask 14'. It is appreciated that depending upon the optics and the size of the electrical component to be ablated, that only a single ablation step or greater than two ablation steps may be necessary in accordance with this disclosure. Further, it is appreciated that instead of multiple masks, that multiple fields may be formed on the same mask in accordance with this disclosure.

Specifically, a second non-limiting example of a suitable ablation apparatus 10' (FIG. 19) is a customized laser system commercially available from LPKF Laser Electronic GmbH, of Garbsen, Germany, which incorporates a Lambda STEEL (Stable Energy Excimer Laser) laser system commercially available from Lambda Physik AG, Göttingen, Germany and a chromium-plated quartz mask commercially available from International Phototool Company, Colorado Springs, Co. The laser system features up to 1000 mJ pulse energy at a wavelength of 308 nm. Further, the laser system has a frequency of 100 Hz. The apparatus 10' may be formed to produce biosensors with two passes as shown in FIGS. 17 and 18, but preferably its optics permit the formation of a 10×40 mm pattern in a 25 ns single pass.

While not wishing to be bound to a specific theory, it is believed that the laser pulse or beam 12 that passes through the mask 14, 14', 14" is absorbed within less than 1 μm of the surface 232 on the ribbon 20. The photons of the beam 12 have an energy sufficient to cause photo-dissociation and the rapid breaking of chemical bonds at the metal/polymer interface. It is believed that this rapid chemical bond breaking causes a sudden pressure increase within the absorption region and forces material (metal film 216) to be ejected from the polymer base surface. Since typical pulse durations are around 20-25 nanoseconds, the interaction with the material occurs very rapidly and thermal damage to edges of the conductive material 216 and surrounding structures is minimized. The resulting edges of the electrical components have high edge quality and accurate placement as contemplated by the present invention.

Fluence energies used to remove or ablate metals from the ribbon 20 are dependent upon the material from which the ribbon 20 is formed, adhesion of the metal film to the base material, the thickness of the metal film, and possibly the process used to place the film on the base material, i.e. supporting and vapor deposition. Fluence levels for gold on KALADEX® range from about 50 to about 90 mJ/cm², on polyimide about 100 to about 120 mJ/cm², and on MELINEX® about 60 to about 120 mJ/cm². It is understood that fluence levels less than or greater than the above mentioned can be appropriate for other base materials in accordance with the disclosure.

Patterning of areas of the ribbon 20 is achieved by using the masks 14, 14'. Each mask 14, 14' illustratively includes a mask field 22 containing a precise two-dimensional illustration of a pre-determined portion of the electrode component patterns to be formed. FIG. 17 illustrates the mask field 22 including contact pads and a portion of traces. As shown in FIG. 18, the second mask 14' contains a second corresponding portion of the traces and the electrode patterns containing fingers. As previously described, it is appreciated that depending upon the size of the area to be ablated, the mask 14 can contain a complete illustration of the entire electrode pattern for each biosensor (FIG. 19), or partial patterns different from those illustrated in FIGS. 17 and 18 in accordance with this disclosure. Preferably, it is contemplated that in one aspect of the present invention, the entire pattern of the electrical components on the test strip are laser ablated at one time, i.e., the broad field encompasses the entire size of the test strip (FIG. 19), or even encompasses the entire size of two or more test strips (not shown). In the alternative, and as illustrated in FIGS. 17 and 18, portions of the entire biosensor are done successively.

While mask 14 will be discussed hereafter, it is appreciated that unless indicated otherwise, the discussion will apply to masks 14', 14" as well. Referring to FIG. 17, areas 24 of the mask field 22 protected by the chrome will block the projection of the laser beam 12 to the ribbon 20. Clear areas or windows 18 in the mask field 22 allow the laser beam 12 to pass through the mask 14 and to impact predetermined areas of the ribbon 20. As shown in FIG. 17, the clear area 18 of the mask field 22 corresponds to the areas of the ribbon 20 from which the conductive material 216 is to be removed.

Further, the mask field 22 has a length shown by line 30 and a width as shown by line 32. Given the imaging ratio of 2:1 of the LPX-200, it is appreciated that the length 30 of the mask is two times the length of a length 34 of the resulting pattern and the width 32 of the mask is two times the width of a width 36 of the resulting pattern on ribbon 20. The optics 16 reduces the size of laser beam 12 that strikes the ribbon 20. It is appreciated that the relative dimensions of the mask field 22 and the resulting pattern can vary in accordance with this disclosure. Mask 14' (FIG. 18) is used to complete the two-dimensional illustration of the electrical components.

Continuing to refer to FIG. 17, in the laser ablation apparatus 10 the excimer laser source 11 emits beam 12, which passes through the chrome-on-quartz mask 14. The mask field 22 causes parts of the laser beam 12 to be reflected while allowing other parts of the beam to pass through in the form of an image of part or all of an electrode pattern. The image or part of laser beam 12 that passes through mask 14 in turn creates a pattern on the gold film where impacted by the laser beam 12. It is appreciated that ribbon or web 20 can be stationary relative to apparatus 10 or move continuously on a roll through apparatus 10. Accordingly, non-limiting rates of movement of the ribbon 20 can be from about 0 m/min to about 100 m/min, more preferably about 30 m/min to about 60 m/min. It is appreciated that the rate of movement of the ribbon 20 is limited only by the apparatus 10 selected and may well exceed 100 m/min depending upon the pulse duration of the laser source 11 in accordance with the present disclosure.

Once the pattern of the mask 14 is created on the ribbon 20, the ribbon is rewound and fed through the apparatus 10 again, with mask 14' (FIG. 18). It is appreciated that laser apparatus 10 could, alternatively, be positioned in series in accordance with this disclosure. A detailed description of the step and repeat process is found in U.S. Application Ser. No. 60/480,397, filed Jun. 20, 2003, entitled "Devices And Methods Relating To Analyte Sensors", the disclosure of which is incorporated herein by reference. Thus, by using masks 14, 14', large areas of the web or ribbon 20 can be patterned using step-and-repeat processes involving multiple mask fields 22 in the same mask area to enable the economical creation of intricate electrode patterns and other electrical components on a substrate of the base, the precise edges of the electrode components, and the removal of greater amounts of the metallic film from the base material.

Figure 20:
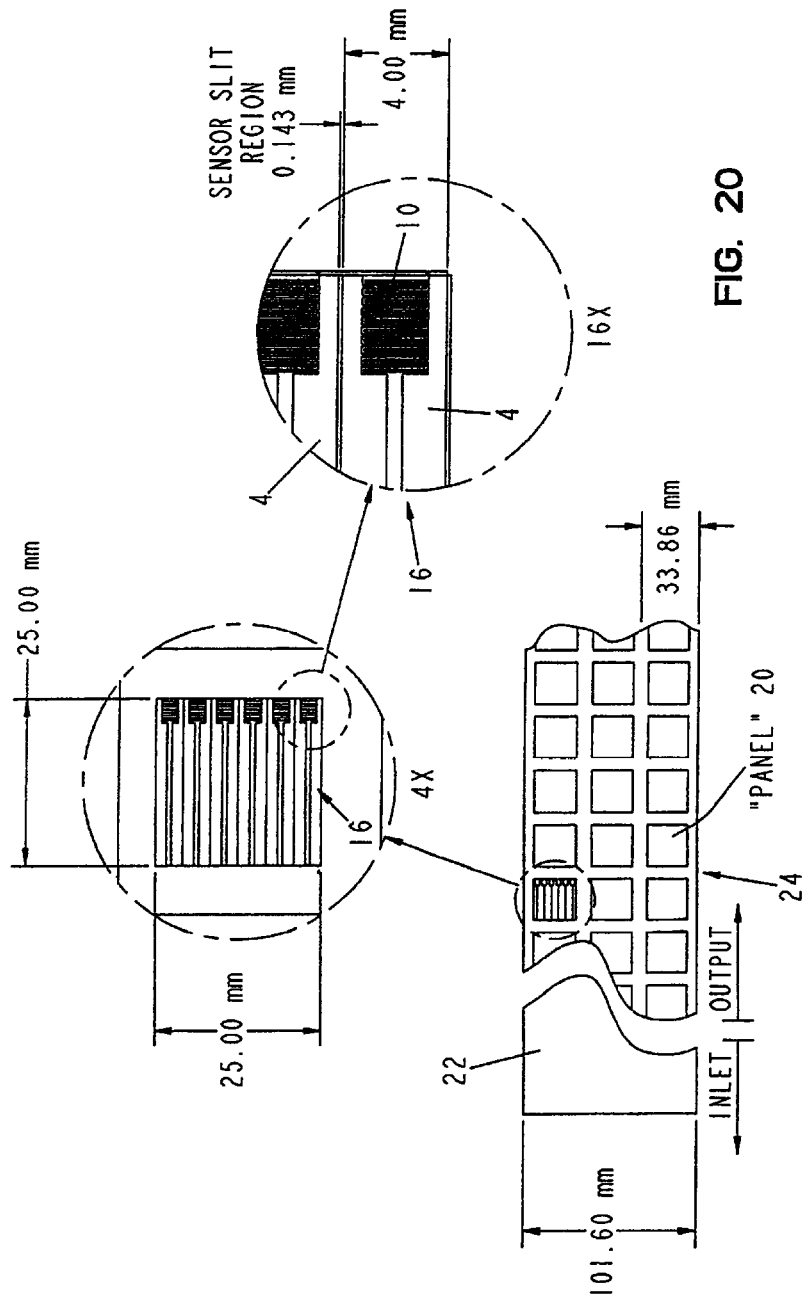
FIG. 20 is a schematic of an electrode set ribbon of the present invention.

FIG. 20 is a non-limiting schematic of an electrode set ribbon 124 formed in accordance with the present disclosure, although having an electrode pattern different from that illustrated in FIGS. 17 and 18. The ribbon 124 includes a plurality of panels 120, each of which includes a plurality of electrode systems 116. Each system includes two electrodes, both labeled 104 and having a sensing region 110. Also shown is the original metallic laminate ribbon 122 that is subject to laser ablation to form the electrode set ribbon 124. The width of the ribbon 122 is selected to accommodate the laser ablation system 10, 10', and may be, for example, 40 to 0.4 inches (1.2 m to 10.25 mm). The ribbon may be any length, and is selected based on the desired number of electrode sets, and/or the ease of handling and transport of the ribbons. The size of each individual panel is selected to fit conveniently on the ribbon, and therefore each panel may contain 1 to 1000 electrode sets, preferably 2 to 20 electrode sets.

Once the complete electrode patterns are created, it is appreciated that the ribbon 20 may be coupled to a spacer and a cover using any number of well-known commercially available methods. A non-limiting example of a suitable method of manufacture, is described in detail in U.S. Application Ser. No. 60/480,397, filed Jun. 20, 2003, entitled "Devices And Methods Relating To Analyte Sensors", the disclosure of which is incorporated herein by reference. In summary, however, it is appreciated that a reagent film is placed upon the ribbon and dried conventionally with an in-line drying system. The rate of processing is nominally 30-38 meters per minute and depends upon the rheology of the reagent. Reagents suitable for the biosensor 210 are given above, but a preferable reagent is set out in Table 2.

The materials are processed in continuous reels such that the electrode pattern is orthogonal to the length of the reel, in the case of the base. Once the base has been coated, the spacer material is laminated onto the coated ribbon 20. Prior to laminating the spacer material, however, a portion of the spacer material is removed, thereby forming a slit. A punching process is used to remove the unneeded portion of the spacer. The die set governs the shape of the slit. The resulting slit-spacer is placed in a reel-to-reel process onto the base. A cover is then laminated onto the spacer using a reel-to reel process. The biosensors can then be produced from the resulting reels of material by means of slitting and cutting.

The slit in the spacer preferably forms a capillary fill space between the base and the cover. A hydrophobic adhesive on the spacer prevents the test sample from flowing into the reagent under the spacer and therefore the fill space defines the test chamber volume. It is appreciated that the chamber volume can vary in accordance with this disclosure depending upon the application of the biosensor. A non-limiting detailed description of suitable fill volumes is found in U.S. Application Ser. No. 60/480,397, noted above.

As discussed above, biosensor 210 has two electrode patterns having different feature sizes on a common planar surface and thus achieves multiple functionalities on that surface. Preferably, electrode set 266 has an electrode pattern formed as a macro electrode array with a first pre-defined feature size. A non-limiting example of a suitable functionality of the macroelectrode array is hematocrit level correction, which is described in U.S. patent application Ser. No. 10/688,312, entitled "System And Method For Analyte Measurement Using AC Phase Angle Measurement", filed Oct. 17, 2003, the disclosure of which is incorporated herein by reference.

Further, it is appreciated that during use, a test meter (not shown) applies a voltage to one electrode and measures the current response at the other electrode to obtain a signal as described in U.S. patent application Ser. No. 10/688,312 just noted.

Electrode set 268 has an electrode pattern formed as an interlaced microelectrode array with a second pre-defined feature size. A non-limiting example of a suitable functionality of the microelectrode array is glucose estimation, which is also described in U.S. patent application Ser. No. 10/688,312. Further, it is appreciated that during use, a test meter (not shown) applies a voltage to one electrode and measures the current response at the other electrode to obtain a signal as described in U.S. patent application Ser. No. 10/688,312.

In operation, a user places his or her lanced finger at opening 221 of biosensor 210. A liquid sample (whole blood) flows from the finger into the opening 221. The liquid sample is transported via capillary action through the sample-receiving chamber 220 and across the fingers 280 of the element of the electrode set 266. Subsequently, the liquid sample flows through the sample-receiving chamber 220 toward vent 262 and into engagement with the reagent 264 situated upon the fingers 284 of the element of the electrode set 268. As discussed above, hematocrit correction values are determined from the interaction of the liquid sample with the fingers 280 and a glucose determination from the interaction of the liquid sample/reagent mixture with the fingers 284. While hematocrit and glucose determination functionalities are described with reference to biosensor 210, it is appreciated that the electrode patterns, may be used for a variety of functionalities in accordance with the present disclosure.

The processes and products described include disposable biosensors, especially for use in diagnostic devices. However, also included are electrochemical biosensors for non-diagnostic uses, such as measuring an analyte in any biological, environmental, or other, sample. In addition, it is appreciated that various uses and available functions of the biosensor may stand alone or be combined with one another in accordance with this disclosure.

As discussed below with reference to FIGS. 11-16, each of the disclosed biosensors operates from the standpoint of a user in a manner similar to that described above with reference from 210. In addition, like components of the biosensors are numbered alike.

Figure 11:
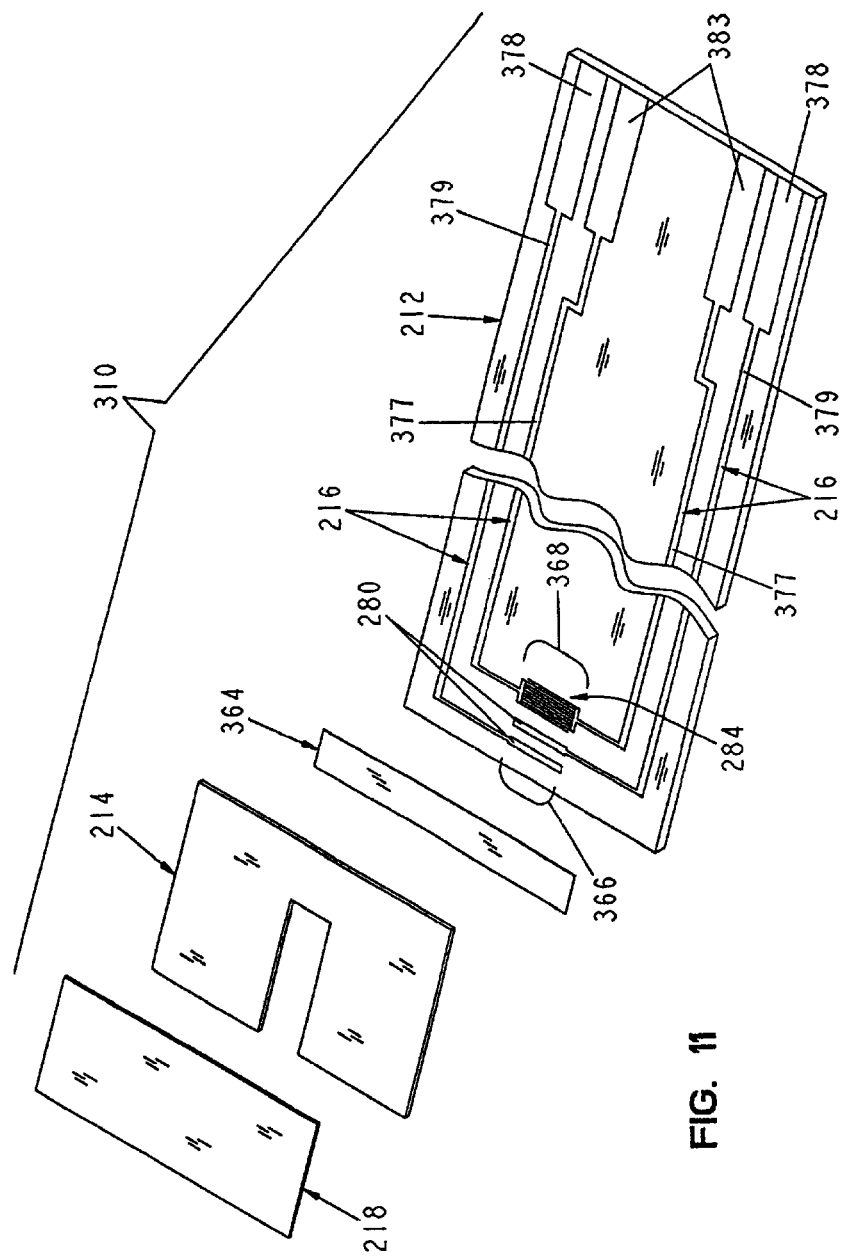
FIG. 11 is an exploded assembly view of a biosensor in accordance with another embodiment of the invention.

Referring now to FIG. 11, a biosensor 310 is formed and manufactured in a manner similar to biosensor 210 except for the pattern of the conductive material 216 positioned on the base 212. The conductive material 216 of biosensor 310 defines a first electrode system 366 and a second electrode system 368. The electrode systems 366, 368 are similar to the systems of biosensor 210 except for the resulting pattern of the connecting traces 377, 379 and contact pads 378, 383 on the base 212. It is submitted that the traces 377, 379 and pads 378, 383 may take on a variety of shapes and sizes in accordance with this disclosure.

Figure 12:
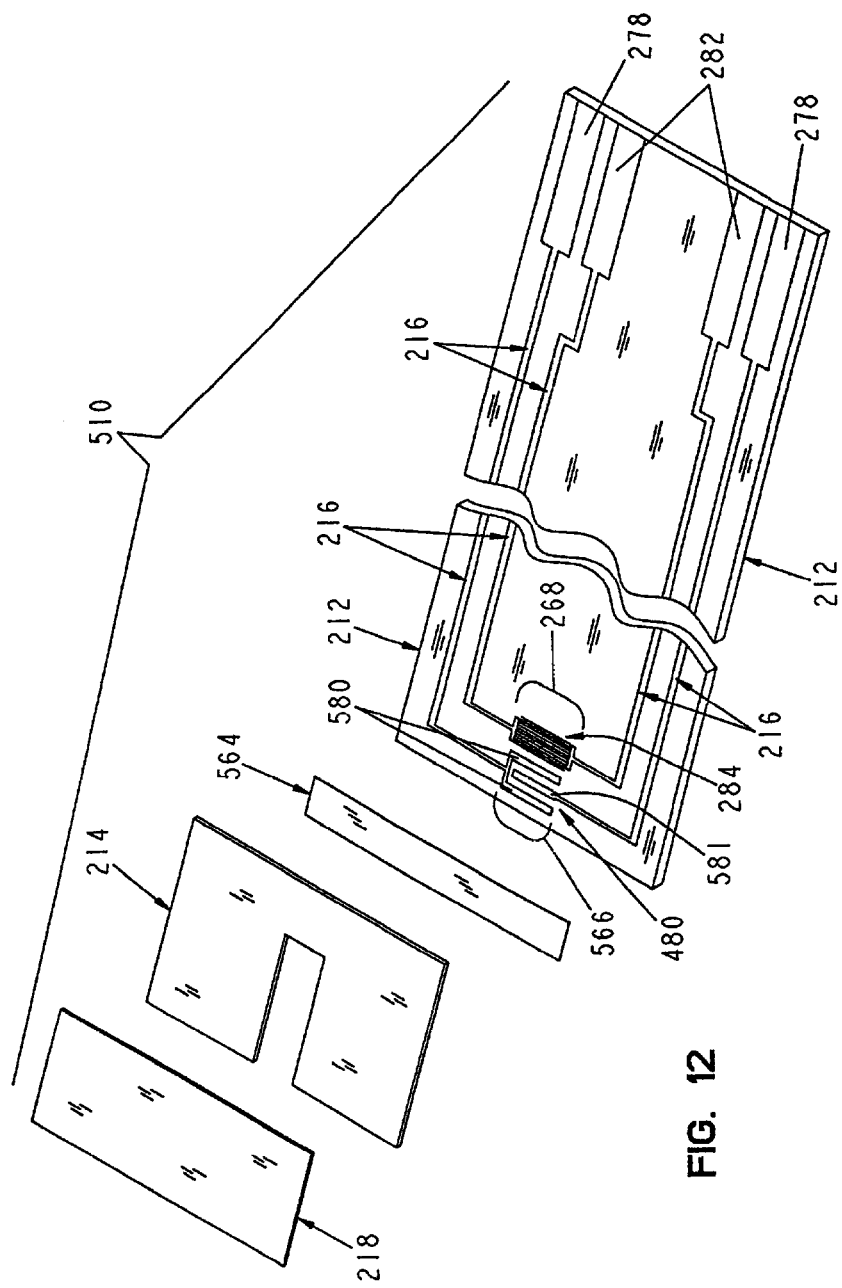
FIG. 12 is an exploded assembly view of a biosensor in accordance with another embodiment of the invention.

As shown in FIG. 12, a biosensor 510 is formed in a manner similar to biosensor 210 except for the pattern of the conductive material 216 positioned on the base 212. In addition to electrode set 268, the conductive material 216 of biosensor 510 defines a first electrode set 566. The electrode set 566 is similar to set 366 except for the configuration of the interlacing electrode pattern formed by the elements of the electrodes.

Specifically, the first electrode set 566 includes a working electrode having an element with one electrode finger 581 and a counter electrode having an element with two electrode fingers 580. The fingers 580, 581 cooperate with one another to create an interlaced electrode pattern configured as a macroelectrode array having a feature size or gap width of about 250 µm. The electrodes 580, 581 each have an electrode width of about 250 µm. As discussed above with set 266, the electrode and gap widths may vary in accordance with this disclosure.

As described above with reference to biosensor 210, the first and second electrode sets 566, 268 have different feature sizes and are used to create different functionalities on biosensor 510. A non-limiting example of a suitable functionality of the first electrode set 566 is for determining correction factors for hematocrit levels. The measurement methods are as discussed above with reference to biosensor 210.

Figure 13:
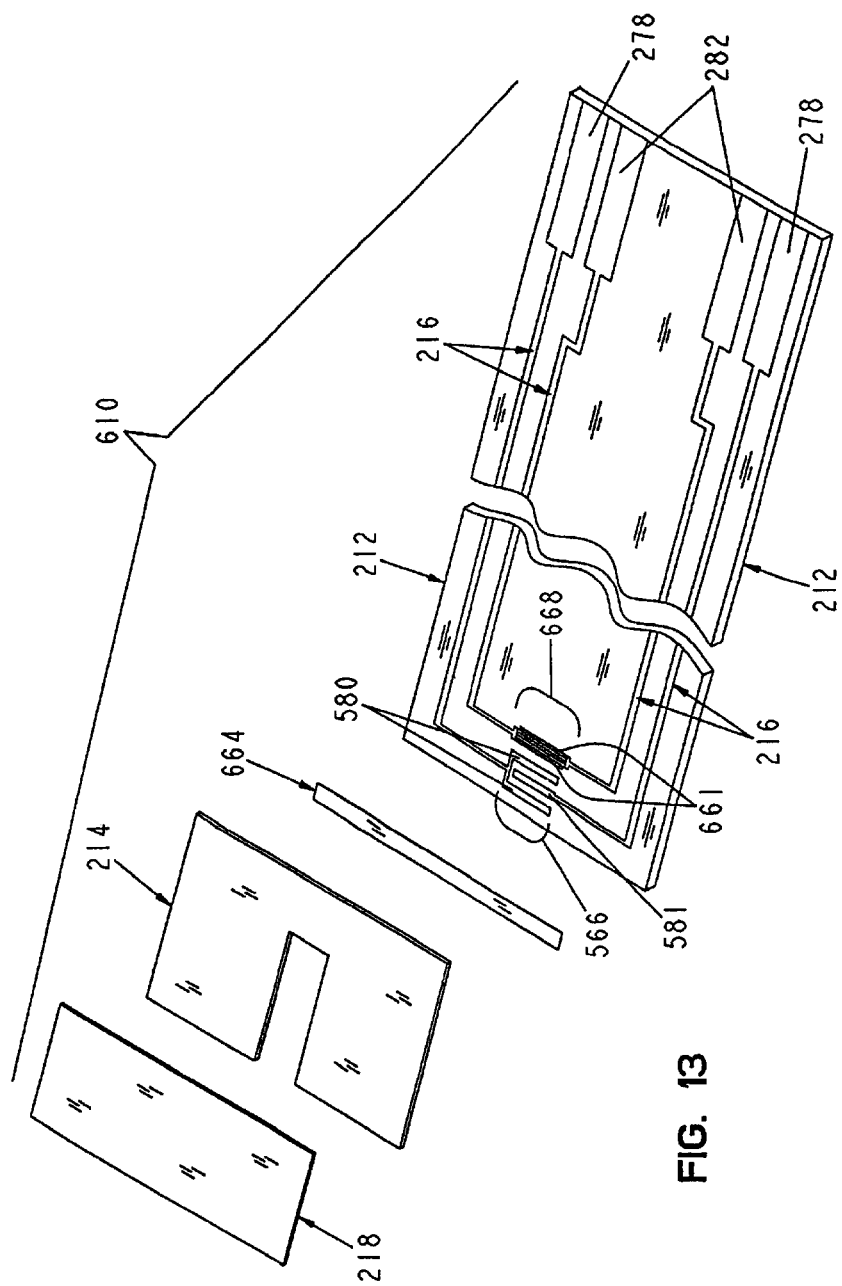
FIG. 13 is an exploded assembly view of a biosensor in accordance with another embodiment of the invention.

Referring now to FIG. 13, a biosensor 610 is formed in a manner similar to biosensor 210 except for the pattern of the conductive material 216 positioned on the base 212. In addition to the first electrode set 566 as discussed above, the conductive material 216 of biosensor 610 defines a second electrode set 668 spaced-apart from set 566.

The electrode set 668 is similar to set 268 except for the pattern of interlacing electrode pattern in the element of the electrodes. Specifically, the second electrode set 668 includes a working electrode and a counter electrode, each having an element with three electrode fingers 661. The fingers 661 cooperate with one another to define an interlaced electrode pattern configured as a microelectrode array having a feature size or gap width of about 50 µm, which is less than the feature size of the electrode pattern of the set 566. The electrodes 661 each have an electrode width of about 50 µm. As discussed above with set 268, the electrode and gap widths may vary in accordance with this disclosure.

In addition, biosensor 610 includes a reagent 664. Reagent 664 is similar to reagent 264, and only differs in its width as it is applied onto the base 212. Specifically, the reagent 664 extends across electrode fingers 661. A non-limiting example of a suitable functionality of the second electrode set 668 is a glucose determination functionality. The measurement methods are as discussed above with reference to biosensor 210.

Figure 14:
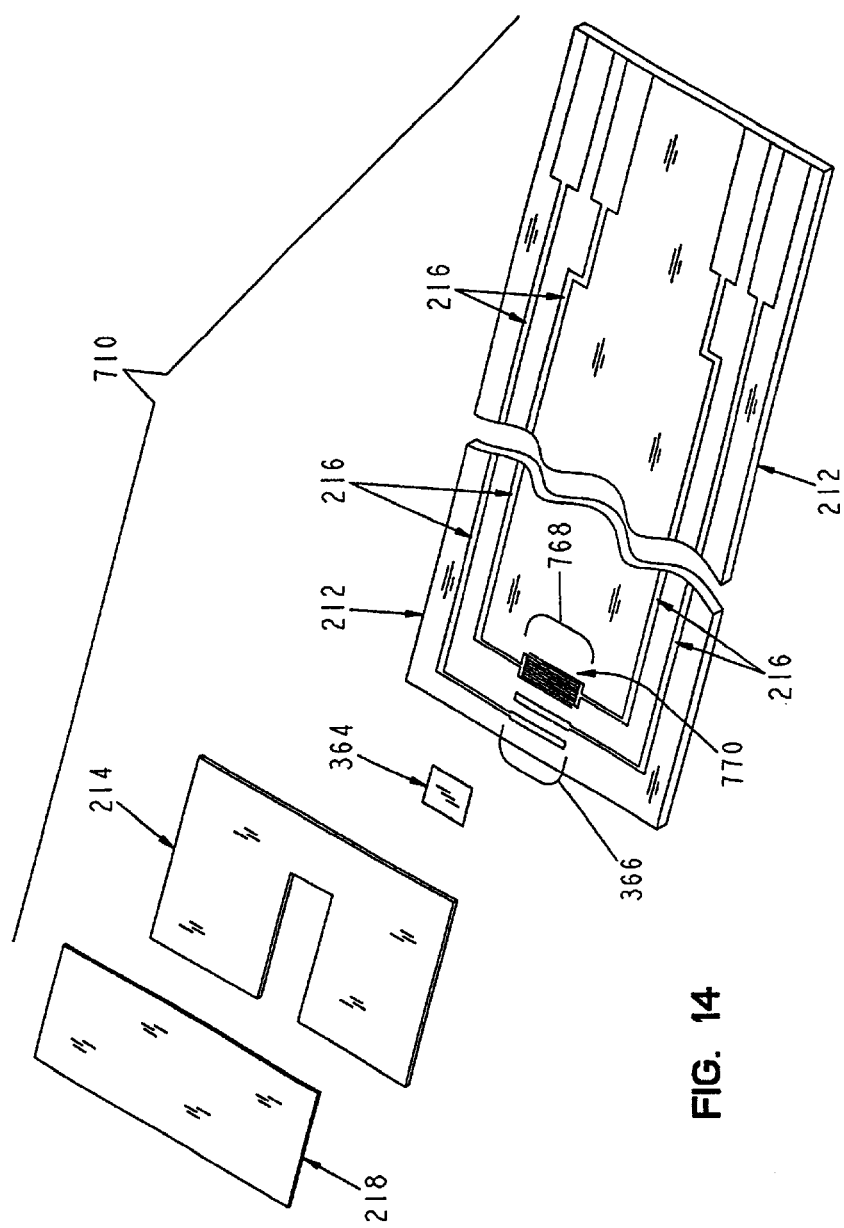
FIG. 14 is an exploded assembly view of a biosensor in accordance with another embodiment of the invention.

As shown in FIG. 14, a biosensor 710 is formed in a manner similar to biosensor 210 except for the pattern of the conductive material 216 positioned on the base 212. The conductive material 216 of biosensor 710 defines the first electrode set 366 as discussed above and a second electrode set 768. The electrode set 768 is similar to set 268 except for the pattern of an interlacing electrode pattern formed by the element of the electrodes. Specifically, the second electrode set 768 includes a working electrode and a counter electrode, each having element with five electrode fingers 770. The fingers 770 cooperate with one another to define an interlaced electrode pattern configured as a microelectrode array having a feature size or gap width of about 30 µm, which is less than the feature size of electrode pattern of set 366. The electrode fingers 770 each have an electrode width of about 50 µm. As discussed above with set 266, the electrode and gap widths may vary in accordance with this disclosure. A non-limiting example of a suitable functionality of the second electrode set 668 is a glucose determination functionality. The measurement methods are as discussed above with reference to biosensor 210.

In addition, biosensor 710 includes a reagent 364 that is dispensed upon the fingers 770 by any of a variety of dispensing methods that are well known to those skilled in the art. Reagent 364 is preferably the reagent set forth in Table 3. Moreover, it is appreciated that a variety of reagents, non-limiting examples of which have been discussed above, may be used in accordance with this disclosure.

Figure 15:
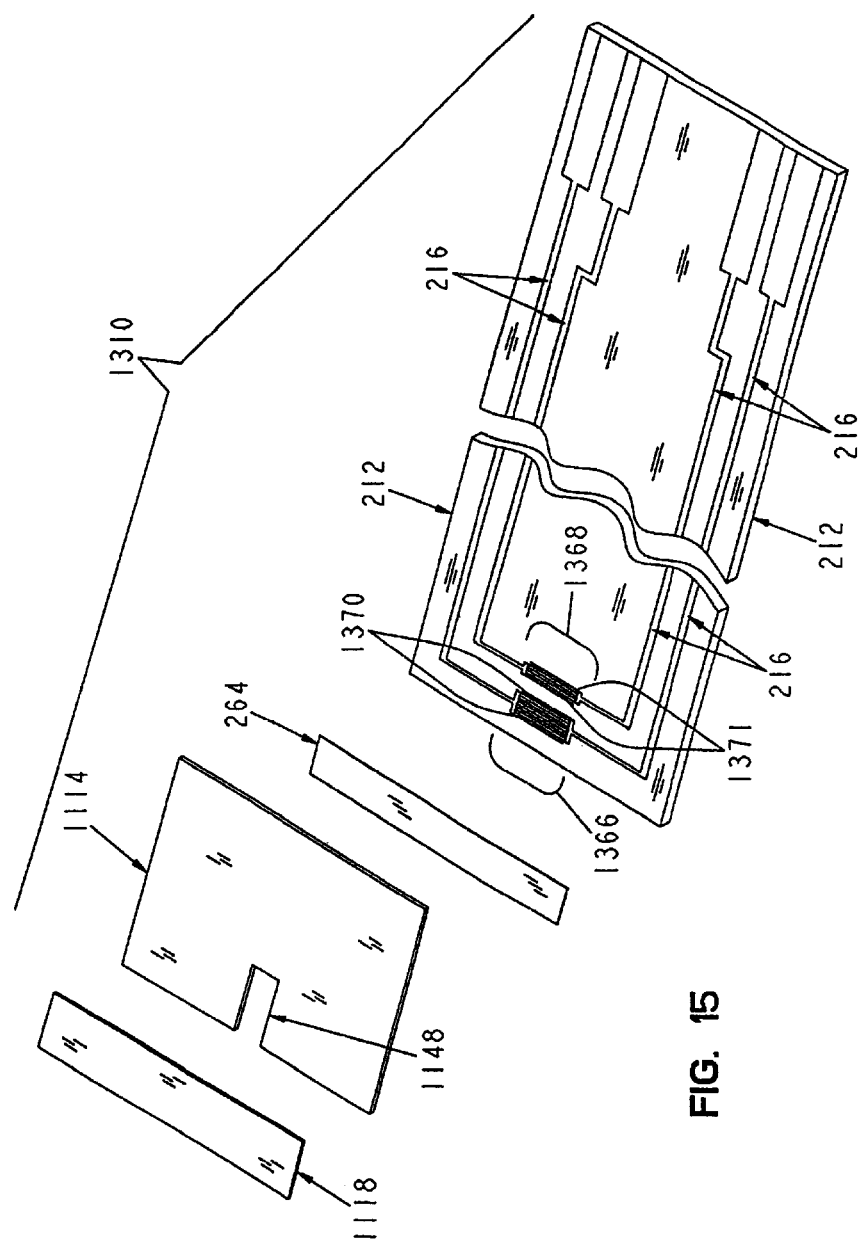
FIG. 15 is an exploded assembly view of a biosensor in accordance with another embodiment of the invention.

FIG. 15 illustrates a biosensor 1310 in accordance with this disclosure. Biosensor 1310 is formed in a manner similar to biosensor 210 except for the configuration of the conductive material 216 positioned on the base 212, the cover 1118, and the spacer 1114. The cover 1118 and spacer 1114 are similar to cover 218 and spacer 214 except for their dimensions relative to the base 212 as shown in FIG. 15. The conductive material 216 of biosensor 1310 defines a first electrode set 1366 and a second electrode set 1368. The first electrode set 1366 includes a working electrode and a counter electrode, each having five electrode fingers 1370. The fingers 1370 cooperate with one another to define an interlaced electrode pattern formed as a microelectrode array having a feature size or gap width of about 17 μm. The electrode fingers 1370 each have an electrode width of about 20 μm.

The second electrode set 1368 includes a working electrode and a counter electrode, each having three electrode fingers 1371. The electrode fingers 1371 cooperate with one another to define an interlaced electrode pattern formed as a microelectrode array having a feature size or gap width of about 10 μm. The electrode fingers 1371 each have an electrode width of about 20 μm. As discussed above with set 266, the electrode and gap widths of fingers 1370 and 1371 may vary in accordance with this disclosure.

The reagent 264 extends across the electrode fingers 1371 of the electrode set 1368. A non-limiting example of a suitable functionality of the first electrode set 1366 includes hematocrit correction as described above with reference to biosensor 210. Likewise, a non-limiting example of a suitable functionality of the second electrode set 1368 is used for determining a glucose estimate as described above with reference to biosensor 210. The method of measurement for the electrode sets, 1366 and 1368 is also as described above with reference to biosensor 210

Figure 24:
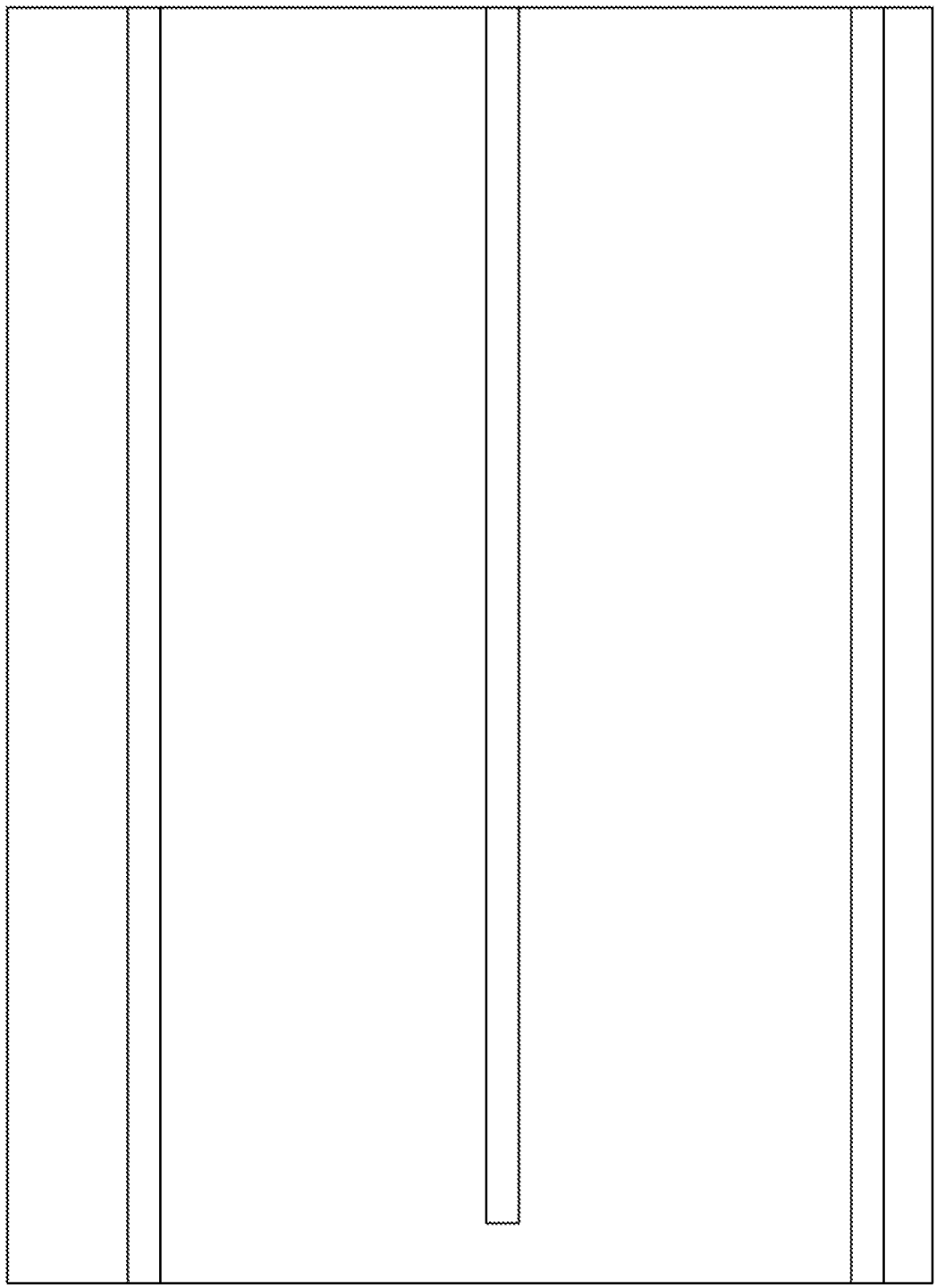
FIG. 24 is a photograph illustrating a biosensor substrate having an electrical pattern with a gap width of approximately 250 μm and where approximately 90% of the conductive material initially covering the substrate has been removed to form the electrical pattern.

FIG. 24 is a photograph of a base substrate having an electrical pattern formed thereon by removing 90% of the conductive material initially covering the base substrate. In this embodiment the conductive material is gold and the gap widths are approximately 250 μm as indicated. The pattern was formed with a single pulse of a laser.

Several production runs were made which demonstrate the very fast speed in which the electrical patterns of the biosensors in accordance with the present invention can be produced. Many of the runs included electrode patterns with two different feature sizes, as indicated in Table 4. FIGS. 21-24 are photos taken of selected ones of the electrode structures, as also indicated in Table 4. The masks used to make the patterns included both "Structure 1" and "Structure 2" listed in Table 4. A single laser pulse of about 25 nanoseconds was used to form the patterns. As indicated, long webs (about 450 m or more) of material were passed under the laser ablation apparatus at a controlled speed as the electrical patterns were formed. The pitch or distance between the electrical patterns was 9.015 mm for all runs, which corresponds to a preferred width of a biosensor made in accordance with the present invention.

TABLE 4

Figure 21:
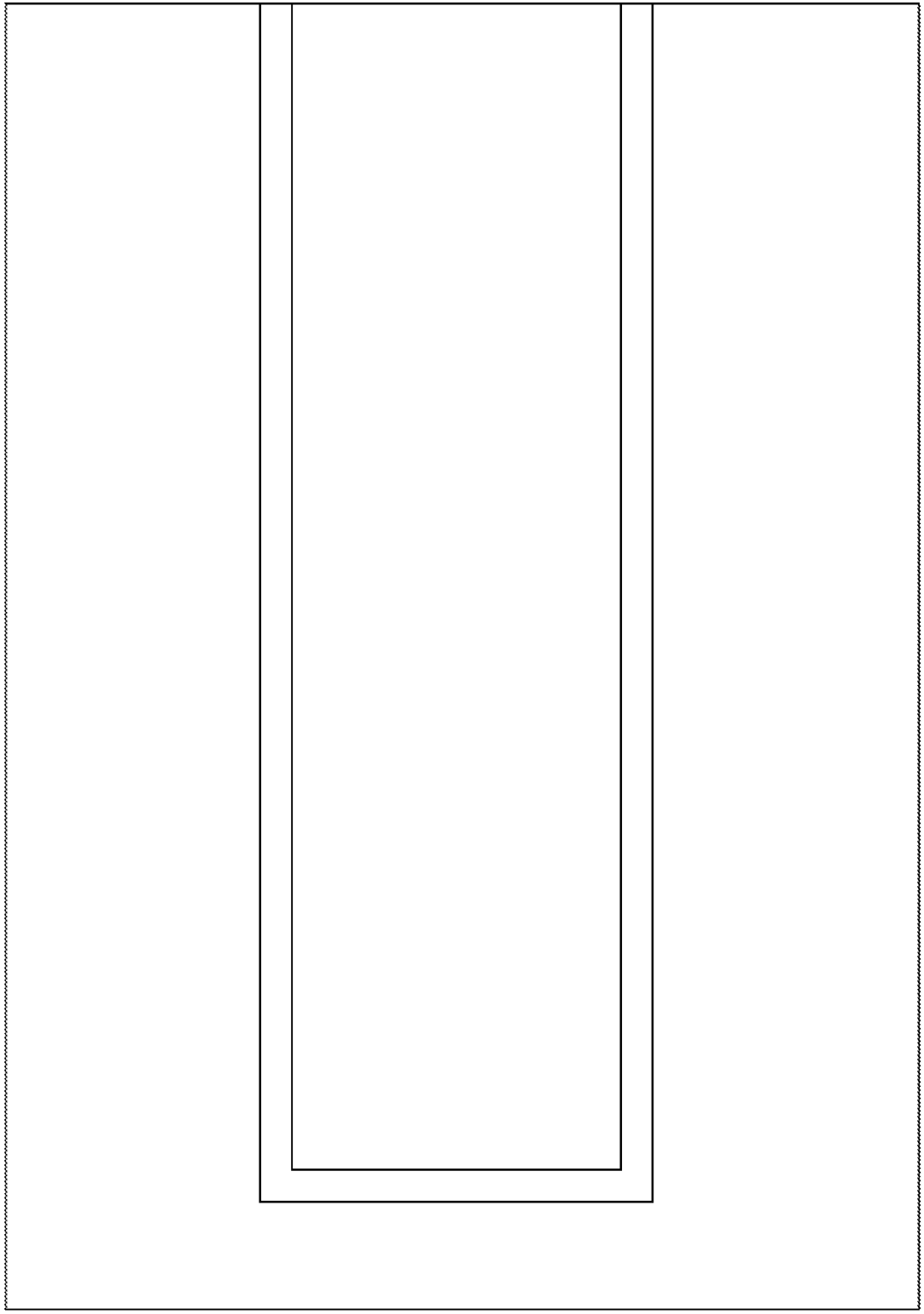
FIG. 21 is a photograph illustrating a biosensor substrate initially coated with a gold conductive layer from which approximately 10% of the conductive material has been removed.
Figure 22:
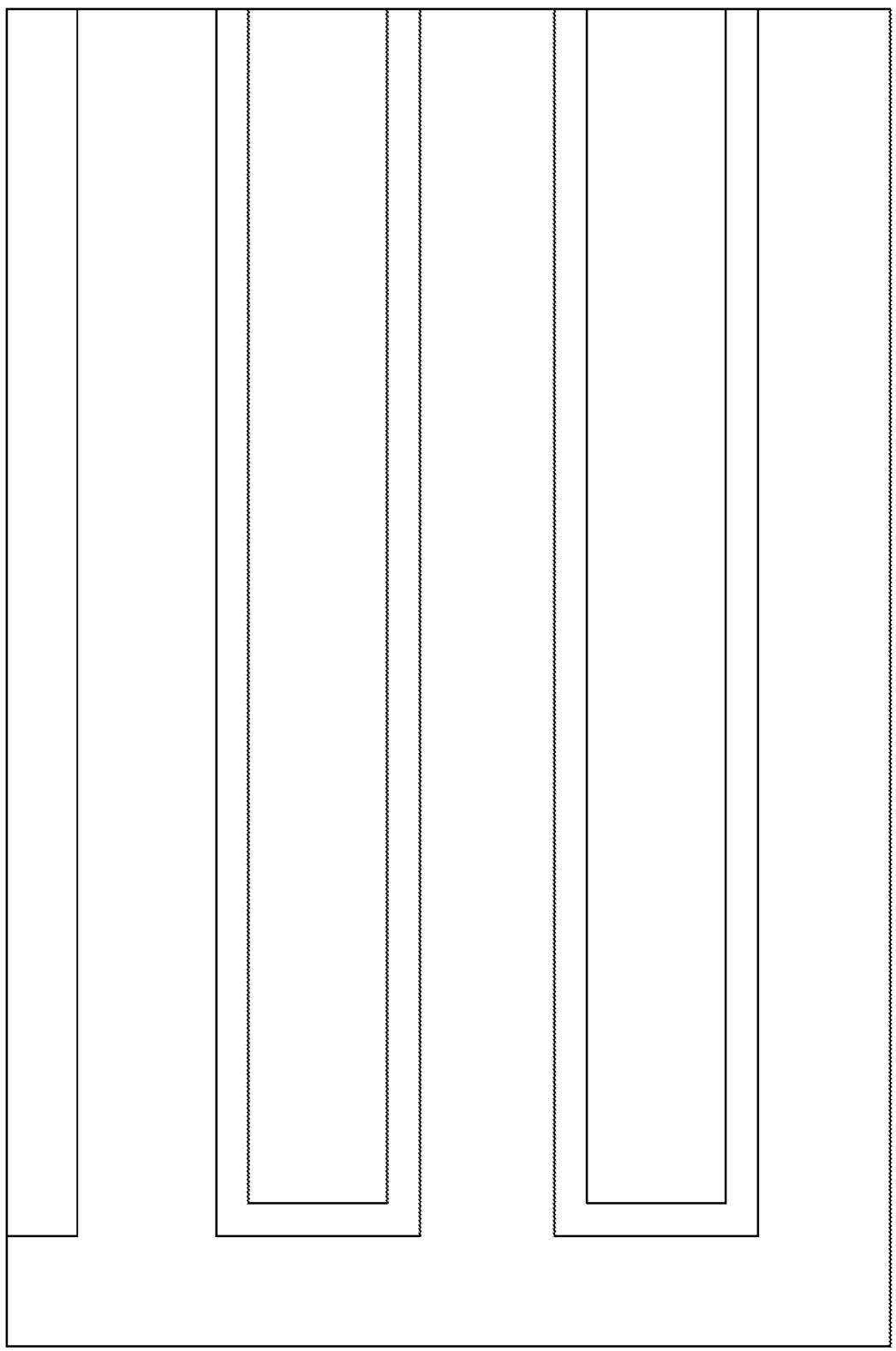
FIG. 22 is a photograph illustrating a biosensor substrate having an electrical pattern with a gap width of approximately 20 μm and where approximately 20% of the conductive material initially covering the substrate has been removed to form the electrical pattern.
Figure 23:
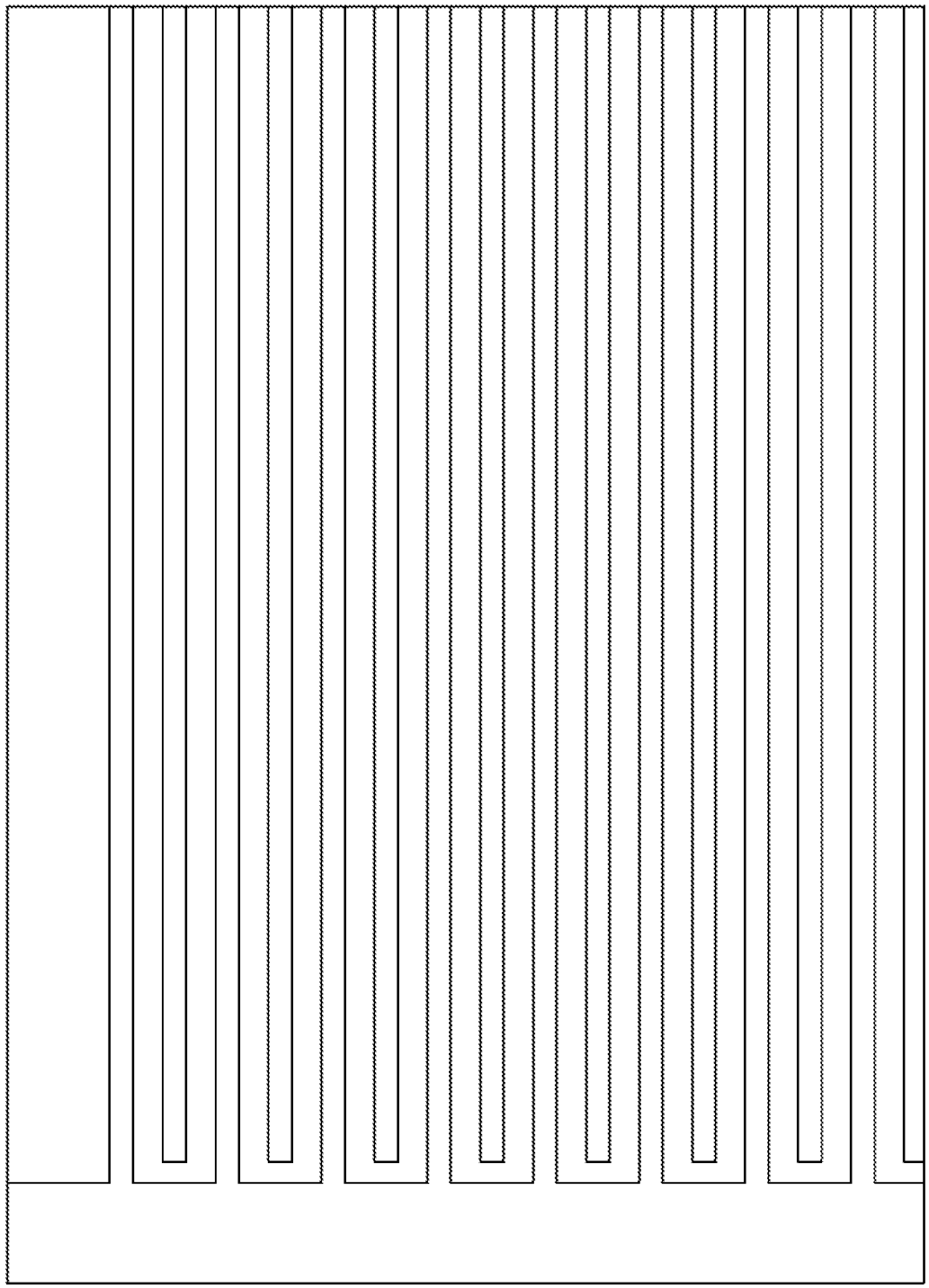
FIG. 23 is a photograph illustrating a biosensor substrate having an electrical pattern with a gap width of approximately 20 μm and where approximately 50% of the of a conductive material initially covering the substrate has been removed to form the electrical pattern.

| Run # | Structure 1 Finger/Gap (μm) | Structure 2 Finger/Gap (μm) | Run time (min) | Patterns per min. | Figure | Roll Length (m) |
|---|---|---|---|---|---|---|
| 1 | 20/20 | 250/200 | 20 | 2585 | | 466 |
| 2 | 250/50 | — | 40 | 1256 | | 453 |
| 3 | 20/250 | 250/20 | 13 | 3873 | 24 (Structure 1) | 454 |
| 4 | 20/20 | 250/20 | 22 | 2284 | FIG. 21 (Structure 2) | 453 |
| 5 | 50/50 | 100/100 | 22 | 2289 | | 454 |
| 6 | 100/50 | — | 20 | 2518 | | 454 |
| 7 | 20/20 | 100/20 | 23 | 2363 | FIG. 23 - Structure 1; FIG. 22 - Structure 2 | 490 |
| 8 | 50/100 | — | 19 | 2755 | | 472 |
| 9 | 20/20 | 50/20 | 19 | 2860 | | 490 |

Figure 16:
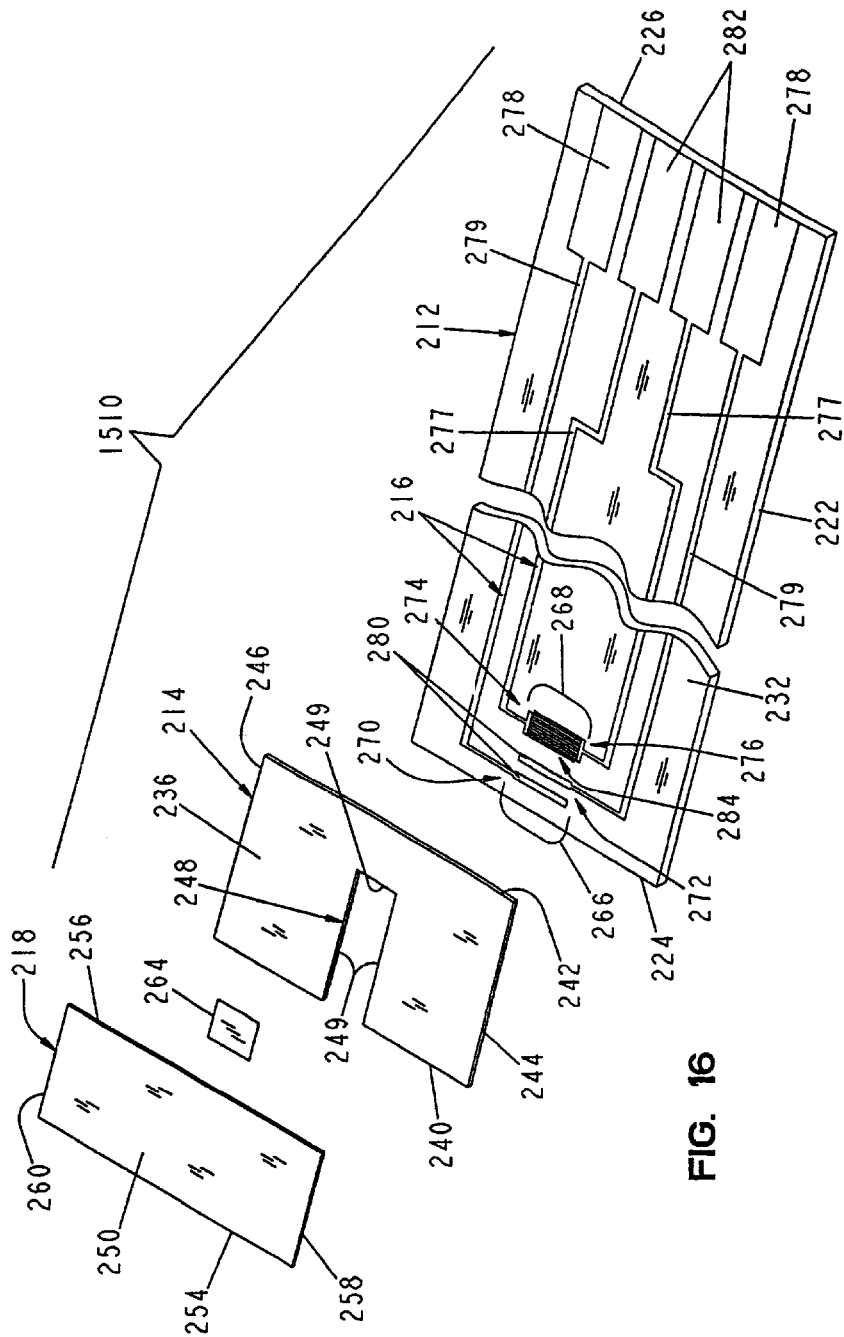
FIG. 16 is an enlarged perspective view of a biosensor in accordance with another embodiment of the invention.

FIG. 16 illustrates biosensor 1510. Biosensor 1510 is identical to biosensor 210, except for the reagent 1564. Reagent 364 is dispensed onto the electrode fingers 284 as discussed above with reference to biosensor 710 of FIG. 14.

FIGS. 21-24 are photographs of electrical patterns formed using the principles of the present invention. FIG. 21 is a photograph of a base substrate having an electrical pattern formed thereon by removing 10% of the conductive material initially covering the base substrate. In this embodiment the conductive material is gold. The pattern was formed with a single pulse of a laser.

FIG. 22 is a photograph of a base substrate having an electrical pattern formed thereon by removing 20% of the conductive material initially covering the base substrate. In this embodiment the conductive material is gold and the gap widths are approximately 20 μm as indicated. The pattern was formed with a single pulse of a laser.

FIG. 23 is a photograph of a base substrate having an electrical pattern formed thereon by removing 50% of the conductive material initially covering the base substrate. In this embodiment the conductive material is gold and the gap widths are approximately 20 μm as indicated. The pattern was formed with a single pulse of a laser.

The "patterns per minute" column reflects the speed at which substrates for individual biosensors can be formed. For example, in Run No. 1, 2585 base substrates each corresponding to a single biosensor, and each having two (2) electrode feature sizes, are formed in a single minute. As can be seen from the above table 4, the method embodied by the present invention is well suited to fast mass production.

Although the invention has been described in detail with reference to a preferred embodiment, variations and modifications exist within the scope and spirit of the invention, on as described and defined in the following claims.

What is claimed is:

1. A method of making a plurality of biosensors having first and second electrode elements formed on each of the plurality of biosensors, said plurality of biosensors being produced by:
    (a) providing a web of base substrate material having a metal conductive layer formed thereon;
    (b) projecting an image of an electrode pattern onto the metal conductive layer with a laser apparatus, wherein an electrode pattern that corresponds to the image is formed by laser ablation on the web of base substrate material, the electrode pattern comprising first and second electrode elements having first and second respective edges defining a gap there between, the gap having a width and a length, wherein each of the first and second edges are spaced from first and second theoretical lines, respectively, by a distance that varies along the length of the gap, the theoretical lines defining desired shape and placement of the first and second edges, wherein the standard deviation of the each of the distances is less than about 6 μm over the entire length of the gap;

(c) moving the web of base substrate material and repeating step (b) a plurality of times to produce a plurality of the electrode patterns at spaced intervals along the web of base substrate material;

(d) depositing a reagent on the web of base substrate material and at least partially covering each electrode pattern of the plurality of electrode patterns with the reagent;

(e) laminating at least one web of a covering layer or a spacing layer over the web of base substrate material, thereby forming a cover and a sample-receiving chamber for each biosensor; and (f) cutting through the at least one web of a covering layer or a spacing layer and the web of base substrate material to form the plurality of biosensors.

2. The method of making a plurality of biosensors of claim 1, wherein the electrode pattern formed in step (b) comprises a complete electrode pattern for one of the biosensors, wherein the complete electrode pattern for each biosensor is formed in a single step.

3. The method of making a plurality of biosensors of claim 2, wherein forming the electrode patterns comprises removing at least 20% of the metal conductive layer.

4. The method of making a plurality of biosensors of claim 1, wherein the electrode pattern formed in step (b) comprises a partial electrode pattern, the image comprises a plurality of the same or different images, and steps (b) and (c) are repeated until the plurality of electrode patterns comprises a plurality of complete electrode patterns, wherein each complete electrode pattern is formed in multiple steps.

5. The method of making a plurality of biosensors of claim 1, wherein the electrode pattern includes at least two electrode sets having different feature sizes.

6. The method of making a plurality of biosensors of claim 1, wherein step (e) comprises:
laminating the spacing layer over the base substrate material, the spacing layer having a void that defines the perimeter of the sample-receiving chamber; and
laminating the covering layer over the spacing layer.

7. The method of making a plurality of biosensors of claim 1, wherein each electrode pattern formed in step (b) is formed in less than 1 second.

8. A method of making a plurality of biosensors having first and second electrode elements formed on each of the plurality of biosensors, said plurality of biosensors being produced by:

(a) providing a web of base substrate material having a metal conductive layer formed thereon;

(b) projecting an image of an electrode pattern onto the metal conductive layer with a laser apparatus, wherein an electrode pattern that corresponds to the image is formed by laser ablation on the web of base substrate material;

(c) moving the web of base substrate material and repeating step (b) a plurality of times to produce a plurality of the electrode patterns at spaced intervals along the web of base substrate material;

(d) depositing a reagent on the web of base substrate material and at least partially covering each electrode pattern of the plurality of electrode patterns with the reagent, the reagent being applied in a substantially continuous stripe;

(e) laminating at least one web of a covering layer or a spacing layer over the web of base substrate material, thereby forming a cover and a sample-receiving chamber for each biosensor; and (f) cutting through the at least one web of a covering layer or a spacing layer and the web of base substrate material to form the plurality of biosensors.

9. The method of making a plurality of biosensors of claim 8, wherein each electrode pattern formed in step (b) comprises the entire electrode pattern for one of the biosensors and each entire electrode pattern is formed all at once.

10. The method of making a plurality of biosensors of claim 8, wherein step (e) comprises:
laminating the spacing layer over the base substrate material, the spacing layer having a void that defines the perimeter of the sample-receiving chamber; and
laminating the covering layer over the spacing layer.

11. The method of making a plurality of biosensors of claim 10, wherein each electrode pattern formed in step (b) is formed in less than 1 second.

* * * * *

UNITED STATES PATENT AND TRADEMARK OFFICE
CERTIFICATE OF CORRECTION

PATENT NO. : 8,551,308 B2  
APPLICATION NO. : 12/238101  
DATED : October 8, 2013  
INVENTOR(S) : Raghbir S. Bhullar Page 1 of 1

It is certified that error appears in the above-identified patent and that said Letters Patent is hereby corrected as shown below:

In the Drawings;

Delete Figs. 21-24 and substitute therefor Figs. 21-24 as shown here.

FIG. 21 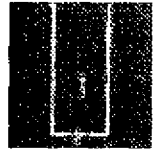

FIG. 22 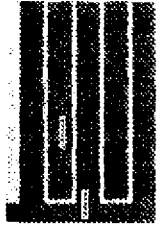

FIG. 23 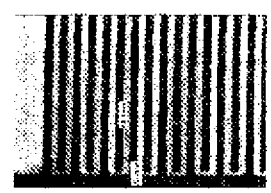

FIG. 24 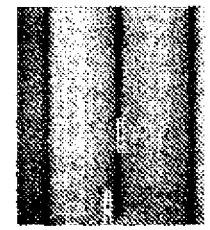

Signed and Sealed this  
Eighteenth Day of February, 2014

Michelle K. Lee  
*Deputy Director of the United States Patent and Trademark Office*